(12) United States Patent
Pierce

(10) Patent No.: US 9,313,962 B2
(45) Date of Patent: Apr. 19, 2016

(54) CELERY CULTIVAR ADS-26

(71) Applicant: A. DUDA & SONS, INC., Oviedo, FL (US)

(72) Inventor: Lawrence K. Pierce, Aromas, CA (US)

(73) Assignee: A. Duda & Sons, Inc., Oviedo, FL (US)

( * ) Notice: Subject to any disclaimer, the term of this patent is extended or adjusted under 35 U.S.C. 154(b) by 233 days.

(21) Appl. No.: 14/061,902

(22) Filed: Oct. 24, 2013

(65) Prior Publication Data
US 2015/0121558 A1    Apr. 30, 2015

(51) Int. Cl.
*A01H 5/04* (2006.01)
*C12N 15/82* (2006.01)

(52) U.S. Cl.
CPC ........................................ *A01H 5/04* (2013.01)

(58) Field of Classification Search
None
See application file for complete search history.

(56) References Cited

U.S. PATENT DOCUMENTS

| | | | |
|---|---|---|---|
| 5,124,505 A | 6/1992 | Orton et al. | |
| 5,304,719 A | 4/1994 | Segebart | |
| 5,367,109 A | 11/1994 | Segebart | |
| 5,523,520 A | 6/1996 | Hunsperger et al. | |
| 5,763,755 A | 6/1998 | Carlone | |
| 5,850,009 A | 12/1998 | Kevern | |
| 7,964,779 B2 * | 6/2011 | Pierce | 800/318 |

OTHER PUBLICATIONS

Jain, M. J. Tissue culture-derived variation in crop improvement. (2001) Euphytica; vol. 118; pp. 153-166.*
Browers & Orton, 1986, Biotechnology in Agriculture and Forestry, vol. 2: Crops 1, Ed, Y.P.S Bajaj, Springer-Verlag, Berlin, Heidelberg, pp. 405-420.
Eshed, et al, 1996, Less-than-additive epistatic interactions of quantitative trait loci in tomato, Genetics, 143:1807-1817.
Kraft, et al, 2000, Linkage disequilibrium and fingerprinting in sugar beet, Theor. Appl. Genet., 101:323-326.
McCarthy, et al., 2001, Commercial celery production in eastern North Carolina, Horticulture Information Leaflet 27, NC State University.
Quiros, et al., 1987, Use of stem proteins and isozymes for the identification of celery varieties, Plant Cell Reports, 6:114-117.

* cited by examiner

*Primary Examiner* — Cathy Kingdon Worley
(74) *Attorney, Agent, or Firm* — Jondle & Associates, P.C.

(57) ABSTRACT

A celery cultivar, designated ADS-26, is disclosed. The invention relates to the seeds of celery cultivar ADS-26, to the plants of celery cultivar ADS-26 and to methods for producing a celery plant by crossing the cultivar ADS-26 with itself or another celery cultivar. The invention further relates to methods for producing a celery plant containing in its genetic material one or more transgenes and to the transgenic celery plants and plant parts produced by those methods. This invention also relates to celery cultivars or breeding cultivars and plant parts derived from celery cultivar ADS-26, to methods for producing other celery cultivars, lines or plant parts derived from celery cultivar ADS-26 and to the celery plants, varieties, and their parts derived from the use of those methods. The invention further relates to hybrid celery seeds, plants, and plant parts produced by crossing cultivar ADS-26 with another celery cultivar.

24 Claims, No Drawings

CELERY CULTIVAR ADS-26

BACKGROUND OF THE INVENTION

The present invention relates to a new and distinctive celery (*Apium graveolens* var. *dulce*) variety, designated ADS-26. All publications cited in this application are herein incorporated by reference.

There are numerous steps in the development of any novel, desirable plant germplasm. Plant breeding begins with the analysis, definition of problems and weaknesses of the current germplasm, the establishment of program goals, and the definition of specific breeding objectives. The next step is selection of germplasm that possesses the traits to meet the program goals. The goal is to combine in a single variety or hybrid an improved combination of desirable traits from the parental germplasm. These important traits may include improved flavor, increased stalk size and weight, higher seed yield, improved color, resistance to diseases and insects, tolerance to drought and heat, and better agronomic quality.

All cultivated forms of celery belong to the species *Apium graveolens* var. *dulce* that is grown for its edible stalk. As a crop, celery is grown commercially wherever environmental conditions permit the production of an economically viable yield. In the United States, the principal growing regions are California, Florida, Arizona and Michigan. Fresh celery is available in the United States year-round, although the greatest supply is from November through January. For planting purposes, the celery season is typically divided into two seasons: summer and winter, with Florida and the southern California areas harvesting from November to July, and Michigan and northern California harvesting from July to October. Celery is consumed as fresh, raw product and as a cooked vegetable.

Celery is a cool-season biennial that grows best from 60° F. to 65° F. (16° C. to 18° C.), but will tolerate temperatures from 45° F. to 75° F. (7° C. to 24° C.). Freezing damages mature celery by splitting the petioles or causing the skin to peel, making the stalks unmarketable. This can be a problem for crops planted in the winter regions; however, celery can tolerate minor freezes early in the season.

The two main growing regions for celery in California are located along the Pacific Ocean: the central coast or summer production area (Monterey, San Benito, Santa Cruz and San Luis Obispo Counties) and the south coast or winter production area (Ventura and Santa Barbara Counties). A minor region (winter) is located in the southern deserts (Riverside and Imperial Counties).

In the south coast, celery is transplanted from early August to April for harvest from November to mid-July; in the Santa Maria area, celery is transplanted from January to August for harvest from April through December. In the central coast, fields are transplanted from March to September for harvest from late June to late December. In the southern deserts, fields are transplanted in late August for harvest in January.

Commonly used celery varieties for coastal production include Tall Utah 52-75, Conquistador and Sonora. Some shippers use their own proprietary varieties. Celery seed is very small and difficult to germinate. All commercial celery is planted as greenhouse-grown transplants. Celery grown from transplants is more uniform than from seed and takes less time to grow the crop in the field. Transplanted celery is traditionally placed in double rows on 40-inch (100-cm) beds with plants spaced between 6.0 and 7.0 inches apart.

Celery requires a relatively long and cool growing season (*The physiology of vegetable crops* by Pressman, CAB Intl., New York, 1997). Earlier transplanting results in a longer growing season, increased yields, and better prices. However, celery scheduled for Spring harvest often involves production in the coolest weather conditions of Winter, a period during which vernalization can occur. If adequate vernalization occurs for the variety, bolting may be initiated. Bolting is the premature rapid elongation of the main celery stem into a floral axis (i.e., during the first year for this normally biennial species). Bolting slows growth as the plant approaches marketable size leaves a stalk with no commercial value. Different varieties have different vernalization requirements, but in the presence of bolting, the length of the seed stem can be used as a means of measuring bolting tolerance that exists in each different variety. The most susceptible varieties reach their vernalization requirement earlier and have time to develop the longest seed stems, while the moderately tolerant varieties take longer to reach their vernalization requirement and have less time to develop a seed stem which would therefore be shorter. Under normal production conditions, the most tolerant varieties may not achieve their vernalization requirement and therefore not produce a measurable seed stem.

The coldest months when celery is grown in the United States are December, January and February. If celery is going to reach its vernalization requirements to cause bolting, it is generally younger celery that is exposed to this cold weather window. This celery generally matures in the months of April and May which constitutes what the celery industry calls the bolting or seeder window. The bolting or seeder window is a period where seed stems are generally going to impact the quality of the marketable celery and this is most consistently experienced in celery grown in the Southern California region. The presence of seed stems in celery can be considered a major marketable defect as set forth in the USDA grade standards. If the seed stem is longer than twice the diameter of the celery stalk or eight inches, the celery no longer meets the standards of US Grade #1. If the seed stem is longer than three times the diameter of the celery stalk, the celery is no longer marketable as US Grade #2 (*United States Standards for Grades of Celery*, United States Department of Agriculture, reprinted January 1997).

Celery is an allogamous biennial crop. The celery genome consists of 11 chromosomes. Its high degree of out-crossing is accomplished by insects and wind pollination. Pollinators of celery flowers include a large number of wasp, bee and fly species. Celery is subject to inbreeding depression, which appears to be dependent upon the genetic background as some lines are able to withstand selfing for three or four generations.

Celery flowers are protandrous, with pollen being released 3-6 days before stigma receptivity. At the time of stigma receptivity the stamens will have fallen and the two stigmata unfolded in an upright position. The degree of protandry varies, which makes it difficult to perform reliable hybridization, due to the possibility of accidental selfing.

Celery flowers are very small, which significantly hinders easy removal of individual anthers. Furthermore, different developmental stages of the flowers in umbels make it difficult to avoid uncontrolled pollinations. The standard hybridization technique in celery consists of selecting flower buds of the same size and eliminating the older and younger flowers. Then, the umbellets are covered with glycine paper bags for a 5-10 day period, during which the stigmas become receptive. At the time the flowers are receptive, available pollen or umbellets shedding pollen from selected male parents are rubbed on to the stigmas of the female parent.

Celery plants require a period of vernalization while in the vegetative phase in order to induce seed stalk development. A period of 6-10 weeks at 5° C. to 8° C. when the plants are greater than 4 weeks old is usually adequate. Due to a wide range of responses to the cold treatment, it is often difficult to synchronize crossing, since plants will flower at different times. However, pollen can be stored for 6-8 months at −10° C. in the presence of silica gel or calcium chloride with a viability decline of only 20-40%, thus providing flexibility to perform crosses over a longer time.

For selfing, the plant or selected umbels are caged in cloth bags. These are shaken several times during the day to promote pollen release. Houseflies (*Musca domestica*) can also be introduced weekly into the bags to perform pollinations.

Celery in general is an important and valuable vegetable crop. Thus, a continuing goal of celery plant breeders is to develop stable, high yielding celery cultivars that are agronomically sound to maximize the amount of yield produced on the land. To accomplish this goal, the celery breeder must select and develop celery plants that have the traits that result in superior cultivars.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools, and methods which are meant to be exemplary and illustrative, not limiting in scope. In various embodiments, one or more of the above-described problems have been reduced or eliminated, while other embodiments are directed to other improvements.

According to the invention, there is provided a novel celery cultivar designated ADS-26. This invention thus relates to the seeds of celery cultivar ADS-26, to the plants of celery cultivar ADS-26 and to methods for producing a celery plant by crossing celery ADS-26 with itself or another celery plant, to methods for producing a celery plant containing in its genetic material one or more transgenes and to the transgenic celery plants produced by that method. This invention also relates to methods for producing other celery cultivars derived from celery cultivar ADS-26 and to the celery cultivar derived by the use of those methods. This invention further relates to hybrid celery seeds and plants produced by crossing celery cultivar ADS-26 with another celery line.

In another aspect, the present invention provides regenerable cells for use in tissue culture of celery cultivar ADS-26. The tissue culture will preferably be capable of regenerating plants having essentially all of the physiological and morphological characteristics of the foregoing celery plant, and of regenerating plants having substantially the same genotype as the foregoing celery plant. Preferably, the regenerable cells in such tissue cultures will be callus, protoplasts, meristematic cells, leaves, pollen, embryos, roots, root tips, anthers, pistils, flowers, seeds, petioles and suckers. Still further, the present invention provides celery plants regenerated from the tissue cultures of the invention.

Another aspect of the invention is to provide methods for producing other celery plants derived from celery cultivar ADS-26. Celery cultivars derived by the use of those methods are also part of the invention.

The invention also relates to methods for producing a celery plant containing in its genetic material one or more transgenes and to the transgenic celery plant produced by those methods.

In another aspect, the present invention provides for single gene converted plants of ADS-26. The single transferred gene may preferably be a dominant or recessive allele. Preferably, the single transferred gene will confer such traits as male sterility, herbicide resistance, insect resistance, modified fatty acid metabolism, modified carbohydrate metabolism, resistance for bacterial, fungal, or viral disease, male fertility, enhanced nutritional quality and industrial usage or the transferred gene will have no apparent value except for the purpose of being a marker for variety identification. The single gene may be a naturally occurring celery gene or a transgene introduced through genetic engineering techniques.

The invention further provides methods for developing celery plant in a celery plant breeding program using plant breeding techniques including recurrent selection, backcrossing, pedigree breeding, restriction fragment length polymorphism enhanced selection, genetic marker enhanced selection and transformation. Seeds, celery plants, and parts thereof, produced by such breeding methods are also part of the invention.

In addition to the exemplary aspects and embodiments described above, further aspects and embodiments will become apparent by reference by the study of the following descriptions.

DETAILED DESCRIPTION OF THE INVENTION

In the description and tables which follow, a number of terms are used. In order to provide a clear and consistent understanding of the specification and claims, including the scope to be given such terms, the following definitions are provided:

Allele. An allele is any of one or more alternative form of a gene, all of which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotype of the $F_1$ hybrid.

Bacterial Blight. A bacterial disease of celery caused by *Pseudomonas syringae* pv. *Apii*. The initial symptoms appear on the leaves as small, bright yellow, circular spots. As these enlarge with a yellow halo, they turn to a rust color. As the spots increase in number they merge to eventually kill the leaf tissue. Bacterial blight is favored by cool, wet conditions and at least 10 hours of leaf wetness is required for infection. The disease is spread by water splashes, farm machinery and field workers especially when the foliage is wet.

Black Streak. A physiological disorder in celery plants causing some petioles, when cut, to show "black streaks" in the lower half or throughout the entire length of the petiole, making the entire crop unmarketable. Symptoms can be triggered under field conditions by high temperatures.

Blackheart. Blackheart is due to a lack of movement of sufficient calcium that causes the plant to turn brown and begin to decay at the growing point of the plant. Celery in certain conditions, such as warm weather, grows very rapidly and is incapable of moving sufficient amounts of calcium to the growing point.

Bolting. The premature development of a flowering or seed stalk, and subsequent seed, before a plant produces a food crop. Bolting is typically caused by late planting when temperatures are low enough to cause vernalization of the plants.

Bolting Period. Also known as the bolting or seeder window, and generally occurs in celery that is transplanted from the middle of December through January and matures in April to May. The intensity and actual weeks that bolting may be observed vary from year to year, but it is generally observed in this window.

Bolting Tolerance. The amount of vernalization that is required for different celery varieties to bolt is genetically controlled. Varieties with increased tolerance to bolting require greater periods of vernalization in order to initiate bolting. A comparison of bolting tolerance between varieties can be measured by the length of the flowering or seed stem under similar vernalization conditions.

Brown Stem. A disease caused by the bacterium *Pseudomonas cichorii* that causes petiole necrosis. Brown Stem is characterized by a firm, brown discoloration throughout the petiole.

Celeriac or Root celery (*Apium graveolens* L. var. *rapaceum*). A plant that is related to celery but instead of having a thickened and succulent leaf petiole as in celery, celeriac has an enlarged hypocotyl and upper root that is the edible product.

Celery Heart. The center most interior petioles and leaves of the celery stalk. They are not only the smallest petioles in the stalk, but the youngest as well. Some varieties are considered heartless because they go right from very large petioles to only a couple of very small petioles. The heart is comprised of the petioles that are closest to the meristem of the celery stalk. Most straw and process type varieties have very little heart development.

*Colletotrichum*. One of the most common and important genera of plant-pathogenic fungi. Causes post-harvest rots, and anthracnose spots and blights of aerial plant parts. In celery it is also accompanied by curling of the foliage.

Consumable. Means material that is edible by humans.

Crackstem. The petiole can crack or split horizontally or longitudinally. Numerous cracks in several locations along the petiole are often an indication that the variety has insufficient boron nutrition. A variety's ability to utilize boron is a physiological characteristic which is genetically controlled.

Essentially all the physiological and morphological characteristics. A plant having essentially all the physiological and morphological characteristics of the recurrent parent, except for the characteristics derived from the converted gene.

Feather Leaf. Feather Leaf is a yellowing of the lower leaves and generally occurs in the outer petioles but can also be found on inner petioles of the stalk. These yellowing leaves which would normally remain in the harvested stalk are considered unacceptable. These petioles then have to be stripped off in order to meet USDA standards which effectively decreases the stalk size and yield.

Flare. The lower, generally wider portion of the petiole which is usually a paler green or white.

*Fusarium* Yellows. A fungal soilborne disease caused by *Fusarium oxysporum* f. sp. *apii* Race 2. Infected plants turn yellow and are stunted. Some of the large roots may have a dark brown and a water-soaked appearance. The water-conducting tissue (xylem) in the stem, crown, and root show a characteristic orange-brown discoloration. In the later stages of infection, plants remain severely stunted and yellowed and may collapse. The disease appears most severe during warm seasons, and in heavy, wet soils.

Gene. As used herein, "gene" refers to a segment of nucleic acid. A gene can be introduced into a genome of a species, whether from a different species or from the same species, using transformation or various breeding techniques.

Gross Yield (Pounds/Acre). The total yield in pounds/acre of trimmed celery plants (stalks).

Leaf Celery (*Apium graveolens* L. var. *secalinum*). A plant that has been developed primarily for leaf and seed production. Often grown in Mediterranean climates, leaf celery more closely resembles celery's wild ancestors. The stems are small and fragile and vary from solid to hollow and the leaves are fairly small and are generally bitter. This type is often used for its medicinal properties and spice.

Leaf Margin Chlorosis. A magnesium deficiency producing an interveinal chlorosis which starts at the margin of leaves.

Maturity Date. Maturity in celery can be dictated by two conditions. The first, or true maturity, is the point in time when the celery reaches maximum size distribution, but before defects such as pith, yellowing, Feather Leaf or Brown Stem appear. The second, or market maturity is an artificial maturity dictated by market conditions, i.e, the market requirement may be for 3 dozen sizes so the field is harvested at slightly below maximum yield potential because the smaller sizes are what the customers prefer at that moment.

Muck. Muck is a soil made up primarily of humus drained from swampland. It is used for growing specialty crops, such as onions, carrots, celery, and potatoes.

MUN. MUN refers to the MUNSELL Color Chart which publishes an official color chart for plant tissues according to a defined numbering system. The chart may be purchased from the Macbeth Division of Kollmorgen Instruments Corporation, 617 Little Britain Road, New Windsor, N.Y. 12553-6148.

Petiole. A petiole is the stem or limb of a leaf, the primary portion of the celery consumed.

Petiole depth. The average measurement in millimeters of the depth of the celery petiole at its narrowest point. The petiole depth measurement is taken from the outside of the petiole (which is the part of the petiole that faces the outside of the stalk) and is measured to the inside of the petiole or cup or the inner most point of the petiole that faces the center of the stalk or heart.

Petiole width. The average measurement of the width of the celery petiole in millimeters at its widest point. The measurement is taken from the side or edge of petiole to the opposite side or edge of the petiole. The measurement is taken 90 degrees from petiole depth.

Phthalides. One of the chemical compounds that are responsible for the characteristic flavor and aroma of celery.

Pith. Pith is a sponginess/hollowness/white discoloration that occurs in the petioles of celery varieties naturally as they become over-mature. In some varieties it occurs at an earlier stage causing harvest to occur prior to ideal maturity. Pith generally occurs in the outer, older petioles first. If it occurs, these petioles are stripped off to make grade, which effectively decreases the stalk size and overall yield potential.

Plant Height. The height of the plant from the bottom of the base or butt of the celery plant to the top of the tallest leaf.

Quantitative Trait Loci. Quantitative Trait Loci (QTL) refers to genetic loci that control to some degree, numerically representable traits that are usually continuously distributed.

Regeneration. Regeneration refers to the development of a plant from tissue culture.

Ribbing. The texture of the exterior surface of the celery petiole can vary from smooth to ribby depending on the variety. Ribbing is the presence of numerous ridges that run vertically along the petioles of the celery plant.

Seed Stem. A seed stem is the result of the elongation of the main stem of the celery, which is usually very compressed to almost non-existent, to form the flowering axis. The seed stem or flowering axis can reach several feet in height during full flower. The length of the seed stem is measured as the distance from the top of the basal plate (the base of the seed stem) to its terminus (the terminal growing point).

Single gene converted. Single gene converted or conversion plant refers to plants which are developed by backcrossing, or via genetic engineering, wherein essentially all of the desired morphological and physiological characteristics of a line are recovered in addition to the single gene transferred into the line via the backcrossing technique or via genetic engineering.

Stalk. A stalk is a single celery plant that is trimmed with the top or foliage and the roots removed.

Standard Stem Celery. A more traditional stem celery with moderate joint length, to be utilized and marketed as a whole stalk with 12 to 14 inch cut or for hearts in retail environment.

Stringiness. Stringiness is a physiological characteristic that is generally associated with strings that get stuck between the consumer's teeth. There are generally two sources of strings in celery. One is the vascular bundle which can be fairly elastic and behave as a string. The second is a strip of particularly strong epidermis cells called schlerenchyma which are located on the surface of the ridges of the celery varieties that have ribs.

Suckers. Suckers are auxiliary shoots that form at the base of the stalk or within the auxiliary buds between each petiole. If these shoots form between the petioles of the stalk, several petioles have to be stripped off causing the celery to become smaller and the functional yields to be decreased.

Tall Stem Celery. A stem celery with especially long petioles with primary purpose of being utilized for production of sticks or limbs.

ADS-26 is a very tall process type celery cultivar which produces joints from 42 centimeters to 58 centimeters. ADS-26 surprisingly possesses excellent tolerance to *fusarium* and good tolerance to bolting.

Under severe *fusarium* conditions (Tables 4-6), ADS-26 outperformed all other varieties within its class to which it was compared for plant height, length to joint, and yield (as measured by number and total weight of four inch sticks). The next best performing cultivar under these conditions was ADS-25. ADS-26 is also fairly tolerant to bolting when observed under severe bolting conditions (Tables 7-8). ADS-26 was significantly more tolerant to bolting than ADS-11 and ADS-17 and slightly improved than ADS-18 as measured by the length of the seed stem.

Under relatively unstressed production conditions in Oxnard, Calif. with zero to light *fusarium* and bolting pressure (Tables 2-3), ADS-26 had the tallest plant height, longest joint length and the best yield as measured by the number and weight of four-inch sticks compared to ADS-25, ADS-11 and ADS-18. ADS-26 was very similar to ADS-21 for four inch stick count and weight and length to joint (Table 2). Under Salinas, Calif. production conditions (Table 9), ADS-26 had better length, height and yield compared to ADS-25; however, ADS-17 was the best performer in this summer central California coastal production region.

ADS-26 was particularly susceptible to lodging cause by Santa Ana wind conditions in Oxnard, Calif. The strong winds, which are generally a fall phenomenon, effectively decreased the yield of ADS-26 (Tables 11 and 14). ADS-26 is very tall and appears to be more susceptible to lodging and petiole damage associated with lodging. ADS-26 also appears to be more susceptible to petiole blistering caused by freezing conditions along with the brown stem that often forms in the damaged tissue. The decreased amount of foliage (Table 3) provides less insulation so that the freezing temperatures have the ability to move deeper into the celery stalk and cause more damage to the petioles (Table 12).

When adverse weather conditions were not prevalent ADS-26 did not consistently outperform ADS-25 in large scale productions (Tables 10 and 13). Compared to small research plots where there is no constraint in yield determination based on length (Tables 2-9), the larger scale production grow outs involve the celery being trimmed at 22-24 inches in order to fit 24 inch totes. This can have the effect of reducing yields on occasions since the yield advantage of ADS-26 is partially predicated on being taller than most other varieties (Table 10). In contrast, the yield of ADS-25 produced in similar non-adverse conditions may be not be constrained by the 22 to 24 inch totes since its yield is based on a typically slightly shorter stalk.

Small trial data (Tables 2-9) demonstrates that the best performance of ADS-26 appears to be in November through December and June through July in Oxnard, Calif. during the periods when *fusarium* can severely impact overall yields (yield measured by the four-inch stick counts and weight) of most other varieties. However, based on larger scale production grow outs (Tables 11 and 14) and the resulting impact of Santa Ana winds that can occur in November and December, and freezing conditions which can occur in January and February (Table 12), ADS-26 appears to be best suited to a harvest window from June through July. During this two month window ADS-26 has particular advantages because it has tolerance to both *fusarium* and bolting. In years when the cold weather is occurring late in the season vernalization can trigger bolting in many varieties as late as July. If temperatures are warmer in the late spring *fusarium* can also become a particular problem. ADS-26 has a particular advantage over all other tall celery varieties by having tolerance to both *fusarium* and bolting so its performance is more consistent.

Celery cultivar ADS-26 has the following morphologic and other characteristics (based primarily on data collected in Oxnard, Calif.):

TABLE 1

VARIETY DESCRIPTION INFORMATION

Maturity: 115 days in Oxnard, California
Plant Height: 104.7 cm
Number of Outer Petioles (>40 cm): 13.0
Number of Inner Petioles (<40 cm): 2.5
Stalk Shape: Cylindrical
Stalk Conformation: Compact
Heart Formation: Sparse
Petiole Length (from butt to first joint): 49.8 cm
Petiole Length Class: Long (>30 cm)
Petiole Width (at midpoint): 1.90 cm
Petiole Thickness (at midpoint): 0.88 cm
Cross Section Shape: Cupped
Color (un-blanched at harvest): MUN 5GY 6/6 (Green)
Anthocyanin: Absent
Stringiness: Very slight
Ribbing: Smooth
Glossiness: Glossy
Leaf Blade Color: MUN 5GY 4/4 (Dark green)
Bolting tolerance: Moderate
Adaxial Crackstem (Boron Deficiency): Tolerant
Abaxial Crackstem (Boron Deficiency): Tolerant
Leaf Margin Chlorosis (Magnesium Deficiency): Tolerant
Blackheart (Calcium Deficiency): Tolerant
Pithiness (Nutritional Deficiency): Moderate tolerance
Feather Leaf: Tolerant
Sucker Development: Tolerant
*Fusarium* Yellows, Race 2 (*Fusarium oxysporum*): Good tolerance
Brown Stem: Moderate tolerance This invention is also directed to methods for producing a celery plant by crossing a first parent celery plant with a second parent celery plant, wherein the first parent celery plant or second parent celery plant is celery cultivar ADS-26. Further, both the first parent celery plant and second parent celery plant may be from cultivar ADS-26. Therefore, any breeding methods using celery cultivar ADS-26 are part of this invention, such as selfing, backcrosses, hybrid breeding, and crosses to populations. Any plants produced using celery cultivar ADS-26 as at least one parent are within the scope of this invention.

Additional methods include, but are not limited to, expression vectors introduced into plant tissues using a direct gene transfer method such as microprojectile-mediated delivery, DNA injection, electroporation and the like. More preferably, expression vectors are introduced into plant tissues by using either microprojectile-mediated delivery with a biolistic device or by using *Agrobacterium*-mediated transformation. Transformant plants obtained with the protoplasm of the invention are intended to be within the scope of this invention.

FURTHER EMBODIMENTS OF THE INVENTION

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes." Over the last fifteen to twenty years several methods for producing transgenic plants have been developed, and the present invention, in particular embodiments, also relates to transformed versions of the claimed line.

Plant transformation involves the construction of an expression vector that will function in plant cells. Such a vector consists of DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed celery plants, using transformation methods as described below to incorporate transgenes into the genetic material of the celery plant(s).

Expression Vectors for Celery Transformation: Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the arts, and include, for example, genes that encode for enzymes that metabolically detoxify a selective chemical agent which may be an antibiotic or a herbicide, or genes that encode an altered target which is insensitive to the inhibitor.

One commonly used selectable marker gene for plant transformation is the neomycin phosphotransferase II (nptII) gene, isolated from transposon Tn5, which when placed under the control of plant regulatory signals confers resistance to kanamycin (Fraley et al., *Proc. Natl. Acad. Sci. U.S.A.*, 80:4803 (1983)). Another commonly used selectable marker gene is the hygromycin phosphotransferase gene which confers resistance to the antibiotic hygromycin (Vanden Elzen et al., *Plant Mol. Biol.*, 5:299 (1985)).

Additional selectable marker genes of bacterial origin that confer resistance to antibiotics include gentamycin acetyl transferase, streptomycin phosphotransferase, and aminoglycoside-3'-adenyl transferase, the bleomycin resistance determinant (Hayford et al., *Plant Physiol*. 86:1216 (1988), Jones et al., *Mol. Gen. Genet.*, 210:86 (1987), Svab et al., *Plant Mol. Biol.* 14:197 (1990), Hille et al., *Plant Mol. Biol.* 7:171 (1986)). Other selectable marker genes confer resistance to herbicides such as glyphosate, glufosinate, or bromoxynil (Comai et al., *Nature* 317:741-744 (1985), Gordon-Kamm et al., *Plant Cell* 2:603-618 (1990) and Stalker et al., *Science* 242:419-423 (1988)).

Selectable marker genes for plant transformation that are not of bacterial origin include, for example, mouse dihydrofolate reductase, plant 5-enolpyruvylshikimate-3-phosphate synthase and plant acetolactate synthase (Eichholtz et al., *Somatic Cell Mol. Genet.* 13:67 (1987), Shah et al., *Science* 233:478 (1986), Charest et al., *Plant Cell Rep.* 8:643 (1990)).

Another class of marker genes for plant transformation require screening of presumptively transformed plant cells rather than direct genetic selection of transformed cells for resistance to a toxic substance such as an antibiotic. These genes are particularly useful to quantify or visualize the spatiotemporal expression of a gene and are frequently referred to as reporter genes because they are fused to a gene or gene regulatory sequence. Commonly used genes for screening presumptively transformed cells include α-glucuronidase (GUS), α-galactosidase, luciferase, chloramphenicol, and acetyltransferase (Jefferson, R. A., *Plant Mol. Biol. Rep.* 5:387 (1987), Teeri et al., *EMBO J.* 8:343 (1989), Koncz et al., *Proc. Natl. Acad. Sci. U.S.A.* 84:131 (1987), DeBlock et al., *EMBO J.* 3:1681 (1984)).

In vivo methods for visualizing GUS activity that do not require destruction of plant tissues are available (Molecular Probes publication 2908, IMAGENE GREEN, p. 1-4 (1993) and Naleway et al., *J. Cell Biol.* 115:151a (1991)). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells (Chalfie et al., *Science* 263: 802 (1994)). GFP and mutants of GFP may be used as screenable markers.

Expression Vectors for Celery Transformation: Promoters

Genes included in expression vectors must be driven by a nucleotide sequence comprising a regulatory element, such as a promoter. Several types of promoters are now well known in the arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include those which preferentially initiate transcription in certain tissues, such as leaves, roots, seeds, fibers, xylem vessels, tracheids, or sclerenchyma. These promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters

An inducible promoter is operably linked to a gene for expression in celery. Optionally, the inducible promoter is operably linked to a nucleotide sequence encoding a signal sequence which is operably linked to a gene for expression in celery. With an inducible promoter the rate of transcription increases in response to an inducing agent.

Any inducible promoter can be used in the instant invention. See Ward et al., *Plant Mol. Biol.* 22:361-366 (1993). Exemplary inducible promoters include, but are not limited to, that from the ACEI system which responds to copper (Meft et al., *PNAS* 90:4567-4571 (1993)); In2 gene from maize which responds to benzenesulfonamide herbicide safeners (Hershey et al., *Mol. Gen Genetics* 227:229-237 (1991) and Gatz et al., *Mol. Gen. Genetics* 243:32-38 (1994)) or Tet repressor from Tn10 (Gatz et al., *Mol. Gen. Genetics* 227: 229-237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., *Proc. Natl. Acad. Sci. U.S.A.* 88:0421 (1991).

B. Constitutive Promoters

A constitutive promoter is operably linked to a gene for expression in celery or the constitutive promoter is operably linked to a nucleotide sequence encoding a signal sequence which is operably linked to a gene for expression in celery.

Many different constitutive promoters can be utilized in the instant invention. Exemplary constitutive promoters include, but are not limited to, the promoters from plant viruses such as the 35S promoter from CaMV (Odell et al., *Nature* 313:810-812 (1985) and the promoters from such genes as rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)) and maize H3 histone (Lepetit et al., *Mol. Gen. Genetics* 231:276-285 (1992) and Atanassova et al., *Plant Journal* 2 (3): 291-300 (1992)). The ALS promoter, Xba1/Ncol fragment 5' to the *Brassica napus* ALS3 structural gene (or a nucleotide sequence similarity to said Xba1/Ncol fragment), represents a particularly useful constitutive promoter. See PCT application WO 96/30530.

C. Tissue-specific or Tissue-preferred Promoters

A tissue-specific promoter is operably linked to a gene for expression in celery. Optionally, the tissue-specific promoter is operably linked to a nucleotide sequence encoding a signal sequence which is operably linked to a gene for expression in celery. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., *Science* 23:476-482 (1983) and Sengupta-Gopalan et al., *Proc. Natl. Acad. Sci. U.S.A.* 82:3320-3324 (1985)); a leaf-specific and light-induced promoter such as that from cab or rubisco (Simpson et al., *EMBO J.* 4(11): 2723-2729 (1985) and Timko et al., *Nature* 318:579-582 (1985)); an anther-specific promoter such as that from LAT52 (Twell et al., *Mol. Gen. Genetics* 217:240-245 (1989)); a pollen-specific promoter such as that from Zml3 (Guerrero et al., *Mol. Gen. Genetics* 244:161-168 (1993)) or a microspore-preferred promoter such as that from apg (Twell et al., *Sex. Plant Reprod.* 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art; for example, Becker et al., *Plant Mol. Biol.* 20:49 (1992), Close, P. S., Master's Thesis, Iowa State University (1993), Knox, C., et al., A Structure and Organization of Two Divergent Alpha-Amylase Genes from Barley", *Plant Mol. Biol.* 9:3-17 (1987), Lerner et al., *Plant Physiol.* 91:124-129 (1989), Fontes et al., *Plant Cell* 3:483-496 (1991), Matsuoka et al., *Proc. Natl. Acad. Sci.* 88:834 (1991), Gould et al., *J. Cell. Biol.* 108:1657 (1989), Creissen et al., *Plant J.* 2:129 (1991), Kalderon, et al., A short amino acid sequence able to specify nuclear location, *Cell* 39:499-509 (1984), Steifel, et al., Expression of a maize cell wall hydroxyproline-rich glycoprotein gene in early leaf and root vascular differentiation, *Plant Cell* 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein can then be extracted from a tissue of interest or from total biomass. Protein extraction from plant biomass can be accomplished by known methods which are discussed, for example, by Heney and Orr, *Anal. Biochem.* 114:92-6 (1981).

According to a preferred embodiment, the transgenic plant provided for commercial production of foreign protein is celery. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, *Methods in Plant Molecular Biology and Biotechnology*, CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant line can be transformed with a cloned resistance gene to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. tomato encodes a protein kinase); Mindrinos et al., *Cell* 78:1089 (1994) (Arabidopsis RSP2 gene for resistance to *Pseudomonas syringae*).

B. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxingenes can be purchased from American Type Culture Collection, Manassas, Va., under ATCC Accession Nos. 40098, 67136, 31995 and 31998.

C. A lectin. See, for example, the disclosure by Van Damme et al., *Plant Molec. Biol.* 24:25 (1994), who disclose the nucleotide sequences of several *Clivia miniata* mannose-binding lectin genes.

D. A vitamin-binding protein such as avidin. See PCT application US 93/06487, the contents of which are hereby incorporated by reference. The application teaches the use of avidin and avidin homologues as larvicides against insect pests.

E. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* α-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., *Gene* 116:165 (1992), for disclosure of heterologous expression in plants of a gene coding for a scorpion insectotoxic peptide.

I. An enzyme responsible for a hyperaccumulation of a monoterpene, a sesquiterpene, a steroid, hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained from ATCC Accession Nos. 39637 and 67152. See also Kramer et al., *Insect Biochem. Molec. Biol.* 23:691 (1993), who teach the nucleotide sequence of a cDNA encoding tobacco hornworm chitinase, and Kawalleck et al., *Plant Molec. Biol.* 21:673 (1993), who provide the nucleotide sequence of the parsley ubi4-2 polyubiquitin gene.

K. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

L. A hydrophobic moment peptide. See PCT application WO 95/16776 (disclosure of peptide derivatives of tachyplesin which inhibit fungal plant pathogens) and PCT application WO 95/18855 (teaches synthetic antimicrobial peptides that confer disease resistance), the respective contents of which are hereby incorporated by reference.

M. A membrane permease, a channel former or a channel blocker. For example, see the disclosure of Jaynes et al., *Plant Sci* 89:43 (1993), of heterologous expression of a cecropin-β, lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus.

O. An insect-specific antibody or an immunotoxin derived there from. Thus, an antibody targeted to a critical metabolic function in the insect gut would inactivate an affected enzyme, killing the insect (Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments)).

P. A virus-specific antibody. For example, Tavladoraki et al., *Nature* 366:469 (1993), shows that transgenic plants expressing recombinant antibody genes are protected from virus attack.

Q. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

R. A developmental-arrestive protein produced in nature by a plant. For example, Logemann et al., *Bio/Technology* 10:305 (1992), have shown that transgenic plants expressing the barley ribosome-inactivating gene have an increased resistance to fungal disease.

S. A lettuce mosaic potyvirus (LMV) coat protein gene introduced into *Lactuca sativa* in order to increase its resistance to LMV infection. See Dinant et al., *Molecular Breeding.* 1997, 3: 1, 75-86.

2. Genes that Confer Resistance to an Herbicide:

A. An herbicide that inhibits the growing point or meristem, such as an imidazolinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B. Glyphosate (resistance conferred by mutant 5-enolpyruvlshikimate-3-phosphate synthase (EPSPS) and aroA genes, respectively) and other phosphono compounds such as glufosinate (phosphinothricin acetyl transferase (PAT) and *Streptomyces hygroscopicus* PAT bar genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPS which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. See also Umaballava-Mobapathie in *Transgenic Research.* 1999, 8: 1, 33-44 that discloses *Lactuca sativa* resistant to glufosinate. European Patent Application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a phosphinothricin-acetyl-transferase gene is provided in European Patent Application No. 0 242 246 to Leemans et al. DeGreef et al., *Bio/Technology* 7:61 (1989), describe the production of transgenic plants that express chimeric bar genes coding for phosphinothricin acetyl transferase activity. Examples of genes conferring resistance to phenoxy proprionic acids and cyclohexones, such as sethoxydim and haloxyfop are the Acc1-S1, Acc1-S2 and Acc1-S3 genes described by Marshall et al., *Theor. Appl. Genet.* 83:435 (1992).

C. An herbicide that inhibits photosynthesis, such as a triazine (psbA and gs+ genes) and a benzonitrile (nitrilase gene). Przibilla et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

D. Acetohydroxy acid synthase, which has been found to make plants that express this enzyme resistant to multiple types of herbicides, has been introduced into a variety of plants. See Hattori et al., *Mol. Gen. Genet.* 246:419, 1995. Other genes that confer tolerance to herbicides include a gene encoding a chimeric protein of rat cytochrome P4507A1 and yeast NADPH-cytochrome P450 oxidoreductase (Shiota et al., *Plant Physiol.*, 106:17, 1994), genes for glutathione reductase and superoxide dismutase (Aono et al., *Plant Cell Physiol.* 36:1687, 1995), and genes for various phosphotransferases (Datta et al., *Plant Mol. Biol.* 20:619, 1992).

E. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,837; 5,767,373; and international publication WO 01/12825.

F. Modified bolting tolerance in plants for example, by transferring a gene encoding for gibberellin 2-oxidase (U.S. Pat. No. 7,262,340). Bolting has also been modified using non-transformation methods; see Wittwer, S. H., et al. (1957) *Science.* 126(3262): 30-31; Booij, R. et al., (1995) *Scientia Horticulturae.* 63:143-154; and Booij, R. et al., (1994) *Scientia Horticulturae.* 58:271-282.

3. Genes that Confer or Contribute to a Value-Added Trait, Such as:

A. Increased iron content of the celery, for example by transforming a plant with a soybean ferritin gene as described in Goto et al., *Acta Horticulturae.* 2000, 521, 101-109.

B. Decreased nitrate content of leaves, for example by transforming a celery with a gene coding for a nitrate reductase. See for example Curtis et al., *Plant Cell Report.* 1999, 18: 11, 889-896.

C. Increased sweetness of the celery by transferring a gene coding for monellin, which elicits a flavor 100,000 times sweeter than sugar on a molar basis. See Penarrubia et al., *Biotechnology.* 1992, 10: 561-564.

D. Modified fatty acid metabolism, for example, by transforming a plant with an antisense gene of stearyl-ACP desaturase to increase stearic acid content of the plant. See Knultzon et al., *Proc. Natl. Acad. Sci. USA* 89:2625 (1992).

E. Modified carbohydrate composition effected, for example, by transforming plants with a gene coding for an enzyme that alters the branching pattern of starch. See Shiroza et al., *J. Bacteriol.* 170:810 (1988) (nucleotide sequence of *Streptococcus mutants* fructosyltransferase gene), Steinmetz et al., *Mol. Gen. Genet.* 20:220 (1985) (nucleotide sequence of *Bacillus subtilis* levansucrase gene), Pen et al., *Bio/Technology* 10:292 (1992) (production of transgenic plants that express *Bacillus licheniformis* α-amylase), Elliot et al., *Plant Molec. Biol.* 21:515 (1993) (nucleotide sequences of tomato invertase genes), Søgaard et al., *J. Biol. Chem.* 268:22480 (1993) (site-directed mutagenesis of barley α-amylase gene), and Fisher et al., *Plant Physiol.* 102:1045 (1993) (maize endosperm starch branching enzyme II).

4. Genes that Control Male-Sterility

A. Introduction of a deacetylase gene under the control of a tapetum-specific promoter and with the application of the chemical N—Ac-PPT; see international publication WO 01/29237.

B. Introduction of various stamen-specific promoters; see international publications WO 92/13956 and WO 92/13957.

C. Introduction of the barnase and the barstar genes; see Paul et al., *Plant Mol. Biol.* 19:611-622, 1992).

Methods for Celery Transformation

Numerous methods for plant transformation have been developed, including biological and physical, plant transformation protocols. See, for example, Miki et al., "Procedures for Introducing Foreign DNA into Plants" in Methods in Plant Molecular Biology and Biotechnology, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick B. R. and Thompson, J. E. Eds. (CRC Press, Inc., Boca Raton, 1993) pages 89-119.

A. *Agrobacterium*-Mediated Transformation

One method for introducing an expression vector into plants is based on the natural transformation system of *Agrobacterium*. See, for example, Horsch et al., *Science* 227:1229 (1985), Curtis et al., *Journal of Experimental Botany*. 1994, 45: 279, 1441-1449, Torres et al., *Plant cell Tissue and Organic Culture*. 1993, 34: 3, 279-285, Dinant et al., *Molecular Breeding*. 1997, 3: 1, 75-86. *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of *Agrobacterium* vector systems and methods for *Agrobacterium*-mediated gene transfer are provided by Gruber et al., supra, Miki et al., supra, and Moloney et al., *Plant Cell Reports* 8:238 (1989). See also, U.S. Pat. No. 5,591,616 issued Jan. 7, 1997.

B. Direct Gene Transfer

Several methods of plant transformation collectively referred to as direct gene transfer, have been developed as an alternative to *Agrobacterium*-mediated transformation. A generally applicable method of plant transformation is microprojectile-mediated transformation wherein DNA is carried on the surface of microprojectiles measuring 1 to 4 μm. The expression vector is introduced into plant tissues with a biolistic device that accelerates the microprojectiles to speeds of 300 to 600 m/s which is sufficient to penetrate plant cell walls and membranes. Russell, D. R., et al. *Pl. Cell. Rep.* 12(3, January), 165-169 (1993), Aragao, F. J. L., et al. *Plant Mol. Biol.* 20(2, October), 357-359 (1992), Aragao, F. J. L., et al. *Pl. Cell. Rep.* 12(9, July), 483-490 (1993). Aragao, *Theor. Appl. Genet.* 93: 142-150 (1996), Kim, J.; Minamikawa, T. *Plant Science* 117: 131-138 (1996), Sanford et al., *Part. Sci. Technol.* 5:27 (1987), Sanford, J. C., *Trends Biotech*. 6:299 (1988), Klein et al., *Bio/Technology* 6:559-563 (1988), Sanford, J. C., *Physiol Plant* 7:206 (1990), Klein et al., *Biotechnology* 10:268 (1992).

Another method for physical delivery of DNA to plants is sonication of target cells. Zhang et al., *Bio/Technology* 9:996 (1991). Alternatively, liposome and spheroplast fusion have been used to introduce expression vectors into plants. Deshayes et al., *EMBO J.*, 4:2731 (1985), Christou et al., *Proc Natl. Acad. Sci. U.S.A.* 84:3962 (1987). Direct uptake of DNA into protoplasts using $CaCl_2$ precipitation, polyvinyl alcohol or poly-L-ornithine have also been reported. Hain et al., *Mol. Gen. Genet.* 199:161 (1985) and Draper et al., *Plant Cell Physiol.* 23:451 (1982). Electroporation of protoplasts and whole cells and tissues have also been described. Saker, M.; Kuhne, T. *Biologia Plantarum* 40(4): 507-514 (1997/98), Donn et al., In Abstracts of VIIth International Congress on Plant Cell and Tissue Culture IAPTC, A2-38, p 53 (1990); D'Halluin et al., *Plant Cell* 4:1495-1505 (1992) and Spencer et al., *Plant Mol. Biol.* 24:51-61 (1994). See also Chupean et al., *Biotechnology*. 1989, 7: 5, 503-508.

Following transformation of celery target tissues, expression of the above-described selectable marker genes allows for preferential selection of transformed cells, tissues and/or plants, using regeneration and selection methods now well known in the art.

The foregoing methods for transformation would typically be used for producing a transgenic line. The transgenic line could then be crossed, with another (non-transformed or transformed) line, in order to produce a new transgenic celery line. Alternatively, a genetic trait which has been engineered into a particular celery cultivar using the foregoing transformation techniques could be moved into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

Single-Gene Conversions

When the term celery plant, cultivar or celery line is used in the context of the present invention, this also includes any single gene conversions of that line. The term "single gene converted plant" as used herein refers to those celery plants which are developed by a plant breeding technique called backcrossing wherein essentially all of the desired morphological and physiological characteristics of a cultivar are recovered in addition to the single gene transferred into the line via the backcrossing technique. Backcrossing methods can be used with the present invention to improve or introduce a characteristic into the line. The term "backcrossing" as used herein refers to the repeated crossing of a hybrid progeny back to one of the parental celery plants for that line, backcrossing 1, 2, 3, 4, 5, 6, 7, 8 or more times to the recurrent parent. The parental celery plant which contributes the gene for the desired characteristic is termed the nonrecurrent or donor parent. This terminology refers to the fact that the nonrecurrent parent is used one time in the backcross protocol and therefore does not recur. The parental celery plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original cultivar of interest (recurrent parent) is crossed to a second line (nonrecurrent parent) that carries the single gene of interest to be transferred. The resulting progeny from this cross are then crossed again to the recurrent parent and the process is repeated until a celery plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original line. To accomplish this, a single gene of the recurrent cultivar is modified or substituted with the desired gene from the nonrecurrent parent, while retaining essentially all of the rest of the desired genetic, and therefore the desired physiological and morphological, constitution of the original line. The choice of the particular nonrecurrent parent will depend on the purpose of the backcross; one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new line but that can be improved by backcrossing techniques. Single gene traits may or may not be transgenic, examples of these traits include but are not limited to, male sterility, modified fatty acid metabolism, modified carbohydrate metabolism, herbicide resistance, resistance for bacterial, fungal, or viral disease, insect resistance, enhanced nutritional quality, industrial usage, yield stability and yield enhancement. These genes are generally inherited through the nucleus. Several of these single gene traits are described in U.S. Pat. Nos. 5,777, 196, 5,948,957 and 5,969,212, the disclosures of which are specifically hereby incorporated by reference.

Tissue Culture

Further reproduction of the variety can occur by tissue culture and regeneration. Tissue culture of various tissues of celery and regeneration of plants there from is well known and widely published. For example, reference may be had to Teng et al., *HortScience*. 1992, 27: 9, 1030-1032 Teng et al., *HortScience*. 1993, 28: 6, 669-1671, Zhang et al., *Journal of Genetics and Breeding*. 1992, 46: 3, 287-290, Webb et al., *Plant Cell Tissue and Organ Culture*. 1994, 38: 1, 77-79, Curtis et al., *Journal of Experimental Botany*. 1994, 45: 279, 1441-1449, Nagata et al., *Journal for the American Society for Horticultural Science*. 2000, 125: 6, 669-672, and Ibrahim et al., Plant Cell, Tissue and Organ Culture. (1992), 28(2): 139-145. It is clear from the literature that the state of the art is such that these methods of obtaining plants are routinely used and have a very high rate of success. Thus, another aspect of this invention is to provide cells which upon growth and differentiation produce celery plants having the physiological and morphological characteristics of variety ADS-26.

As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers and the like. Means for preparing and maintaining plant tissue culture are well known in the art. By way of example, a tissue culture comprising organs has been used to produce regenerated plants. U.S. Pat. Nos. 5,959,185, 5,973,234 and 5,977,445 describe certain techniques, the disclosures of which are incorporated herein by reference.

Additional Breeding Methods

This invention also is directed to methods for producing a celery plant by crossing a first parent celery plant with a second parent celery plant wherein the first or second parent celery plant is a celery plant of cultivar ADS-26. Further, both first and second parent celery plants can come from celery cultivar ADS-26. Thus, any breeding methods using celery cultivar ADS-26 are part of this invention, such as selfing, backcrosses, hybrid production, crosses to populations, and the like. All plants produced using celery cultivar ADS-26 as at least one parent are within the scope of this invention, including those developed from cultivars derived from celery cultivar ADS-26. Advantageously, this celery cultivar could be used in crosses with other, different, celery plants to produce the first generation ($F_1$) celery hybrid seeds and plants with superior characteristics. The cultivar of the invention can also be used for transformation where exogenous genes are introduced and expressed by the cultivar of the invention. Genetic variants created either through traditional breeding methods using celery cultivar ADS-26 or through transformation of cultivar ADS-26 by any of a number of protocols known to those of skill in the art are intended to be within the scope of this invention.

The following describes breeding methods that may be used with celery cultivar ADS-26 in the development of further celery plants. One such embodiment is a method for developing cultivar ADS-26 progeny celery plants in a celery plant breeding program comprising: obtaining the celery plant, or a part thereof, of cultivar ADS-26 utilizing said plant or plant part as a source of breeding material, and selecting a celery cultivar ADS-26 progeny plant with molecular markers in common with cultivar ADS-26 and/or with morphological and/or physiological characteristics selected from the characteristics listed in Table 1. Breeding steps that may be used in the celery plant breeding program include pedigree breeding, backcrossing, mutation breeding, and recurrent selection. In conjunction with these steps, techniques such as RFLP-enhanced selection, genetic marker enhanced selection (for example SSR markers) and the making of double haploids may be utilized.

Another method involves producing a population of celery cultivar ADS-26 progeny celery plants, comprising crossing cultivar ADS-26 with another celery plant, thereby producing a population of celery plants, which, on average, derive 50% of their alleles from celery cultivar ADS-26. A plant of this population may be selected and repeatedly selfed or sibbed with a celery cultivar resulting from these successive filial generations. One embodiment of this invention is the celery cultivar produced by this method and that has obtained at least 50% of its alleles from celery cultivar ADS-26.

One of ordinary skill in the art of plant breeding would know how to evaluate the traits of two plant varieties to determine if there is no significant difference between the two traits expressed by those varieties. For example, see Fehr and Walt, *Principles of Cultivar Development*, p 261-286 (1987). Thus the invention includes celery cultivar ADS-26 progeny celery plants comprising a combination of at least two cultivar ADS-26 traits selected from the group consisting of those listed in Table 1 or the cultivar ADS-26 combination of traits listed in the Summary of the Invention, so that said progeny celery plant is not significantly different for said traits than celery cultivar ADS-26 as determined at the 5% significance level when grown in the same environmental conditions. Using techniques described herein, molecular markers may be used to identify said progeny plant as a celery cultivar ADS-26 progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of celery cultivar ADS-26 may also be characterized through their filial relationship with celery cultivar ADS-26, as for example, being within a certain number of breeding crosses of celery cultivar ADS-26. A breeding cross is a cross made to introduce new genetics into the progeny, and is distinguished from a cross, such as a self or a sib cross, made to select among existing genetic alleles. The lower the number of breeding crosses in the pedigree, the closer the relationship between celery cultivar ADS-26 and its progeny. For example, progeny produced by the methods described herein may be within 1, 2, 3, 4 or 5 breeding crosses of celery cultivar ADS-26.

Choice of breeding or selection methods depends on the mode of plant reproduction, the heritability of the trait(s)

being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences the choice of breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, the overall value of the advanced breeding lines, and the number of successful cultivars produced per unit of input (e.g., per year, per dollar expended, etc.).

Promising advanced breeding lines are thoroughly tested and compared to appropriate standards in environments representative of the commercial target area(s) for at least three years. The best lines are candidates for new commercial cultivars; those still deficient in a few traits are used as parents to produce new generations for further selection.

These processes, which lead to the final step of marketing and distribution, usually take from ten to twenty years from the time the first cross or selection is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of celery plant breeding is to develop new, unique and superior celery cultivars. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same celery traits.

Each year, the plant breeder selects the germplasm to advance to the next generation. This germplasm is grown under unique and different geographical, climatic and soil conditions and further selections are then made, during and at the end of the growing season. The cultivars that are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he/she develops, except possibly in a very gross and general fashion. The same breeder cannot produce the same line twice by using the exact same original parents and the same selection techniques. This unpredictability results in the expenditure of large research monies to develop superior celery cultivars.

The development of commercial celery cultivars often starts with crosses between different commercial varieties and/or germplasm at different stages in development. Pedigree breeding and recurrent selection breeding methods are used to develop cultivars from breeding populations. Breeding programs combine desirable traits from two or more varieties or various broad-based sources into breeding pools from which cultivars are developed by selfing and selection of desired phenotypes. The new cultivars are crossed with other varieties and the hybrids from these crosses are evaluated to determine which have commercial potential.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals usually begins in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

In the strictest sense, the single-seed descent procedure refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In addition to phenotypic observations, the genotype of a plant can also be examined. There are many laboratory-based techniques available for the analysis, comparison and characterization of a plants genotype. Among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

Isozyme Electrophoresis and RFLPs have been widely used to determine genetic composition. Shoemaker and Olsen, (*Molecular Linkage Map of Soybean* (*Glycine max*) p. 6.131-6.138 in S. J. O'Brien (ed) Genetic Maps: Locus Maps of Complex Genomes, Cold Spring Harbor Laboratory Press, Cold Spring Harbor, N.Y., (1993)) developed a molecular genetic linkage map that consisted of 25 linkage groups with about 365 RFLP, 11 RAPD, three classical markers and four isozyme loci. See also, Shoemaker, R. C., *RFLP Map of Soybean*, p 299-309, in Phillips, R. L. and Vasil, I. K., eds. *DNA-Based Markers in Plants*, Kluwer Academic Press, Dordrecht, the Netherlands (1994).

SSR technology is currently the most efficient and practical marker technology; more marker loci can be routinely used and more alleles per marker locus can be found using SSRs in comparison to RFLPs. For example, Diwan and Cregan described a highly polymorphic microsatellite locus in soybean with as many as 26 alleles. (Diwan, N. and Cregan, P. B., *Theor. Appl. Genet.* 95:22-225, 1997.) SNPs may also be used to identify the unique genetic composition of the invention and progeny varieties retaining that unique genetic composition. Various molecular marker techniques may be used in combination to enhance overall resolution.

Molecular markers, which include markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a back-crossing breeding program. The markers can also be used to select toward the genome of the recurrent parent and against the markers of the donor parent. This procedure attempts to minimize the genomic contribution from the donor parent that remains in the selected plants, and can reduce the number of back-crosses necessary to generate coisogenic plants. This procedure is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding is another method of introducing new traits into celery varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), alkylating agents (such as sulfur mustards, nitrogen mustards, epoxides, ethyleneamines, sulfates, sulfonates, sulfones, or lactones), azide, hydroxylamine, nitrous acid or acridines. Once a desired phenotype is observed the genetic mutation responsible for that trait may then be incorporated into existing germplasm by traditional breeding techniques. Details of mutation breeding can be found in *Principles of Cultivar Development* by Fehr, Macmillan Publishing Company, 1993.

The production of double haploids can also be used for the development of homozygous varieties in a breeding program. Double haploids are produced by doubling a set of chromosomes from a heterozygous plant to produce a completely homozygous individual. For example, see Wan et al., *Theor. Appl. Genet.*, 77:889-892, 1989.

Descriptions of other breeding methods that are commonly used for different traits and crops can be found in several reference books (e.g., *Principles of Plant Breeding* John Wiley and Son, pp. 115-161, 1960; Allard, 1960; Simmonds, 1979; Sneep et al., 1979; Fehr, 1987; A Carrots and Related Vegetable Umbelliferae@, Rubatzky, V. E., et al., 1999).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

As used herein, the term "plant" includes plant cells, plant protoplasts, plant cell tissue cultures from which celery plants can be regenerated, plant calli, plant clumps and plant cells that are intact in plants or parts of plants, such as leaves, pollen, embryos, roots, root tips, anthers, pistils, flowers, seeds, petioles, suckers and the like.

Industrial Uses of Celery Cultivar ADS-26

Celery may be used in a variety of manners including but not limited to, use in salads, soups, being filled with cheese, soybean, vegetable, peanut butter or dairy type products, served raw, cooked, baked or frozen, served as sticks, pieces, dices, or dipped like potato chips.

TABLES

In the tables that follow, the traits and characteristics of celery cultivar ADS-26 are given compared to other cultivars.

Table 2 shows a comparison of cultivars ADS-26 with ADS-25, ADS-11, ADS-18 and ADS-21 grown in Oxnard, Calif. under fairly normal conditions for *fusarium* and very slight bolting pressure. Evaluation occurred at 100 days on Jun. 21, 2010 following transplanting Mar. 13, 2010. Table 2, column 1 shows the characteristic, column 2 shows the results for ADS-26, column 3 shows the results for ADS-25, column 4 shows the results for ADS-11, column 5 shows the results for ADS-18 and column 6 shows the results for ADS-21.

TABLE 2

|  |  | ADS-26 | ADS-25 | ADS-11 | ADS-18 | ADS-21 |
|---|---|---|---|---|---|---|
| Plant Height (cm) | Average | 101.4 | 86.4 | 80.4 | 91.1 | 91.6 |
|  | Range | (94-106) | (83-90) | (77-84) | (86-95) | (88-98) |
| Trimmed Plant Weight (kg) | Average | 1.04 | 0.97 | 0.91 | 0.92 | 1.12 |
|  | Range | (0.75-1.46) | (0.66-1.18) | (0.71-1.13) | (0.75-1.14) | (0.76-1.68) |
| Number of Outer Petioles (>40 cm) | Average | 10.7 | 10.5 | 10.2 | 10.5 | 11.1 |
|  | Range | (9-14) | (8-12) | (8-13) | (9-12) | (10-12) |
| Number of Inner Petioles (<40 cm) | Average | 3.9 | 3.1 | 4.0 | 3.4 | 4.1 |
|  | Range | (3-5) | (2-4) | (3-5) | (3-4) | (3-6) |
| Length of Outer Petioles to the joint (cm) | Average | 50.0 | 47.6 | 44.9 | 49.5 | 51.6 |
|  | Range | (47.0-53.7) | (41.7-52.3) | (42.7-47.7) | (45.7-55.0) | (46.0-55.3) |
| Width of Outer Petioles at the midrib (mm) | Average | 20.6 | 20.1 | 21.3 | 20.1 | 21.8 |
|  | Range | (18.0-24.7) | (18.7-21.7) | (19.0-23.0) | (18.0-23.7) | (19.0-26.0) |
| Thickness of Outer Petioles at the midrib (mm) | Average | 9.1 | 8.8 | 9.0 | 8.8 | 9.6 |
|  | Range | (8-10) | (7.7-9.7) | (6.7-10.0) | (8-10) | (6.7-11.7) |
| Number of 4 inch Sticks | Average | 36.3 | 30.5 | 28.0 | 31.9 | 34.7 |
|  | Range | (29.0-44.0) | (25.0-35.0) | (23.0-32.0) | (25.0-39.0) | (29.0-40.0) |
| Weight of 4 inch Sticks (kg) | Average | 0.62 | 0.50 | 0.49 | 0.51 | 0.64 |
|  | Range | (0.43-0.90) | (0.33-0.60) | (0.37-0.61) | (0.38-0.67) | (0.47-0.91) |
| Length of Seed Stems (cm) | Average | 0.0 | 0.2 | 0.2 | 0.0 | 0.0 |
|  | Range | (0-0) | (0-1) | (0.0-1.0) | (0-0) | (0-0) |
|  | Median | 0.0 | 0.0 | 0.0 | 0.0 | 0.0 |
| Petiole Smoothness |  | smooth | smooth | smooth | smooth | smooth - slight rib |
| Petiole Cup |  | cup | cup | cup | cup | cup |

As shown in Table 2, ADS-26 was the considerably taller than other comparison varieties but was most similar to ADS-25 for trimmed weight. The joint length of ADS-26 was comparable to ADS-18 and ADS-21, and yield based on number and weight of four inch sticks was most similar to ADS-21. Except for thinner and narrower petioles ADS-26 was most similar to ADS-21. However, ADS-21 was essentially unharvestable due to pith and ADS-11 was 22% out of grade and 55% borderline for the same issue. ADS-25 and ADS-26 were solid without pith, providing excellent quality stick product. ADS-25 and ADS-11 had very slight and similar bolting initiation compared to each of the other varieties.

Table 3 shows a comparison of cultivars ADS-26, ADS-25, ADS-11 and ADS-18 under fairly normal production conditions in Oxnard, Calif. in the fall of 2010. The trial was transplanted Aug. 16, 2010 and harvested Nov. 12, 2010 at 88 days maturity and grown at a plant population of 49,000 plants per acre. Table 3, column 1 shows the characteristic, column 2 shows the results for ADS-26, column 3 shows the results for ADS-25, column 4 shows the results for ADS-11, and column 5 shows the results for ADS-18.

TABLE 3

|  |  | ADS-26 | ADS-25 | ADS-11 | ADS-18 |
|---|---|---|---|---|---|
| Plant Height (cm) | Average | 105.4 | 85.8 | 82.4 | 90.8 |
|  | Range | (100-112) | (83-89) | (78-88) | (86-95) |
| Top Width (cm) | Average | 23.1 | 31.5 | 38.8 | 33.5 |
|  | Range | (20-25) | (29-34) | (34-45) | (30-37) |
| Trimmed Plant Weight (kg) | Average | 0.95 | 0.75 | 0.86 | 0.87 |
|  | Range | (0.67-1.32) | (0.65-0.85) | (0.75-1.00) | (0.72-1.04) |
| Number of Outer Petioles (>40 cm) | Average | 8.8 | 8.5 | 9.5 | 9.3 |
|  | Range | (8-10) | (8-9) | (9-10) | (8-10) |
| Number of Inner Petioles (<40 cm) | Average | 2.4 | 1.7 | 2.2 | 2.4 |
|  | Range | (2-3) | (1-2) | (1-3) | (2-3) |
| Length of Outer Petioles to the joint (cm) | Average | 53.4 | 46.8 | 44.4 | 49.9 |
|  | Range | (51.0-56.3) | (43.7-48.7) | (41.0-47.0) | (46.0-52.7) |
| Width of Outer Petioles at the midrib (mm) | Average | 17.7 | 16.9 | 18.3 | 18.1 |
|  | Range | (16.7-19.3) | (16.0-18.0) | (17.0-19.7) | (16.7-19.3) |
| Thickness of Outer Petioles at the midrib (mm) | Average | 8.8 | 7.4 | 8.2 | 8.1 |
|  | Range | (8.0-10.0) | (6.3-8.3) | (7.0-9.0) | (7.3-9.0) |
| Number of 4 inch Sticks | Average | 34.3 | 29.8 | 29.8 | 30.6 |
|  | Range | (27-43) | (28-33) | (25-36) | (26-38) |
| Weight of 4 inch Sticks (kg) | Average | 0.55 | 0.41 | 0.46 | 0.49 |
|  | Range | (0.35-0.8) | (0.35-0.48) | (0.37-0.55) | (0.38-0.68) |

As shown in Table 3, ADS-26 has a much taller and narrower and erect foliar presentation compared to ADS-25, ADS-11 and ADS-18. ADS-26 is also longer to the joint and has higher yield than ADS-25, ADS-11 and ADS-18 (as measured by number and weight of four inch sticks and trimmed plant weight).

Table 4 shows a comparison between cultivars ADS-26, ADS-25, ADS-11, ADS-17, ADS-18 and ADS-21 under conditions of severe *fusarium* pressure. This particular trial was grown in a field located in Oxnard, Calif. that has an extremely high level of *Fusarium oxysporum* f. sp. *apii* race 2. The field was developed with especially high *fusarium* levels for the purpose of evaluating varieties for *fusarium* tolerance. This trial was transplanted Aug. 17, 2010 and evaluated Dec. 8, 2010 at 113 days maturity. Table 4, column 1 shows the characteristic, column 2 shows the results for ADS-26, column 3 shows the results for ADS-25, column 4 shows the results for ADS-11, column 5 shows the results for ADS-17, column 6 shows the results for ADS-18 and column 7 shows the results for ADS-21. *Fusarium* ratings are from 0-5, where 0 indicates dead plants and 5 indicates resistant and are presented as a range of expression.

to *fusarium* compared to ADS-11, ADS-17, ADS-18 and ADS-21, and is slightly more tolerant than ADS-25.

Table 5 shows a comparison of cultivars ADS-26, ADS-25, ADS-17, and ADS-21 under conditions of severe *fusarium* pressure. This particular trial was grown in a field located in Oxnard, Calif. that has an extremely high level of *Fusarium oxysporum* f. sp. *apii* race 2. The field was developed with especially high *fusarium* levels for the purpose of evaluating varieties for *fusarium* tolerance. This trial was transplanted Mar. 3, 2011 and evaluated Jul. 1, 2011 at 120 days maturity.

TABLE 4

| | | ADS-26 | ADS-25 | ADS-11 | ADS-17 | ADS-18 | ADS-21 |
|---|---|---|---|---|---|---|---|
| Plant Height (cm) | Average | 95.0 | 81.7 | 71.6 | 62.6 | 81.5 | 71.3 |
| | Range | (89-99) | (80-87) | (66-76) | (53-72) | (70-91) | (65-77) |
| Trimmed Plant | Average | 0.73 | 0.67 | 0.33 | 0.28 | 0.51 | 0.27 |
| Weight (kg) | Range | (0.60-0.86) | (0.45-0.80) | (0.17-0.50) | (0.13-0.49) | (0.15-0.93) | (0.13-0.39) |
| Number of Outer | Average | 9.9 | 9.7 | 6.9 | 6.8 | 7.7 | 6.2 |
| Petioles (>40 cm) | Range | (9-11) | (9-11) | (5-9) | (5-9) | (4-10) | (4-8) |
| Number of Inner | Average | 2.4 | 2.2 | 2.0 | 2.5 | 2.0 | 2.0 |
| Petioles (<40 cm) | Range | (2-3) | (2-3) | (1-3) | (2-4) | (1-3) | (1-3) |
| Length of Outer | Average | 47.1 | 42.5 | 40.0 | 32.3 | 41.1 | 36.0 |
| Petioles to the | Range | (44.0-54.0) | (39.7-45.7) | (37.0-42.3) | (29.3-36.7) | (32.0-45.7) | (30.7-42.7) |
| joint (cm) | | | | | | | |
| Width of Outer | Average | 16.8 | 17.0 | 13.1 | 12.2 | 15.7 | 12.7 |
| Petioles at the | Range | (14.7-18.3) | (15.3-18.3) | (10.3-16.0) | (5.7-17.0) | (11.0-19.7) | (9.3-14.7) |
| midrib (mm) | | | | | | | |
| Thickness of Outer | Average | 8.3 | 8.0 | 7.7 | 7.0 | 8.6 | 6.6 |
| Petioles at the | Range | (7.7-9.3) | (7.3-9.0) | (6.3-9.0) | (5.3-9.0) | (5.7-10.7) | (5.3-7.3) |
| midrib (mm) | | | | | | | |
| Number of 4 inch | Average | 31.8 | 26.5 | 16.1 | 12.7 | 19.7 | 12.5 |
| Sticks | Range | (29-34) | (22-30) | (12-22) | (9-19) | (11-29) | (7-18) |
| Weight of 4 inch | Average | 0.40 | 0.34 | 0.15 | 0.11 | 0.25 | 0.13 |
| Sticks (kg) | Range | (0.32-0.47) | (0.21-0.43) | (0.08-0.23) | (0.04-0.21) | (0.06-0.50) | (0.07-0.22) |
| General *Fusarium* | | 3-4 | 2-4 | 1-3 | 2 | 2-3 | 2 |
| Rating | | | | | | | |
| Root *Fusarium* | | 4-5 | 4-5 | 1-2 | 2-3 | 3-4 | 2-3 |
| Rating | | | | | | | |
| Petiole Color | | 5gy 6/6 | 5gy 6/6 | 5gy 7/6 | 5gy 6/6 | 5gy 6/6 | 5gy 6/6 |
| (Munsell Color | | | | | | | |
| Chart) | | | | | | | |
| Leaf Color | | 5gy 4/4 | 5gy 4/4 | 5gy 4/4 | 5gy 4/4 | 5gy 4/4 | 5gy 4/4 |
| (Munsell Color | | | | | | | |
| Chart) | | | | | | | |
| Petiole Smoothness | | Smooth | Smooth | Slight Rib | Rib | Smooth | Smooth/ Slight Rib |
| Petiole Cup | | Cup | Cup | Slight Cup | Slight Cup | Cup | Cup |

As shown in Table 4, under conditions of severe *fusarium* ADS-26 is taller, produces more overall plant weight, a higher number of outer petioles and longer joints than ADS-11, ADS-17, ADS-18, ADS-21 and ADS-25. ADS-26 also out yields the same varieties for number and total weight of four inch sticks. ADS-26 shows considerable improved tolerance The plant population was 69,696 plants per acre. Table 5, column 1 shows the characteristic, column 2 shows the results for ADS-26, column 3 shows the results for ADS-25, column 4 shows the results for ADS-17, and column 5 shows the results for ADS-21. *Fusarium* ratings are from 0-5, where 0 indicates dead plants and 5 indicates resistant and are presented as a range of expression

TABLE 5

| | | ADS-26 | ADS-25 | ADS-17 | ADS-21 |
|---|---|---|---|---|---|
| Plant Height (cm) | Average | 103.3 | 82.3 | 64.3 | 71.7 |
| | Range | (93-113) | (77-88) | (53-72) | (64-80) |
| Trimmed Plant Weight (kg) | Average | 1.22 | 0.94 | 0.61 | 0.53 |
| | Range | (0.76-1.67) | (0.61-1.35) | (0.25-0.91) | (0.19-0.96) |
| Number of Outer Petioles | Average | 12.3 | 10.2 | 9.5 | 7.7 |
| (>40 cm) | Range | (10-14) | (8-12) | (3-15) | (5-11) |
| Number of Inner Petioles | Average | 3.2 | 3.1 | 5.0 | 2.9 |
| (<40 cm) | Range | (3-4) | (2-4) | (3-10) | (2-5) |
| Length of Outer Petioles to | Average | 45.3 | 43.0 | 36.1 | 36.5 |
| the joint (cm) | Range | (40.7-48.3) | (37.7-45.3) | (26.0-45.0) | (31.3-41.7) |
| Width of Outer Petioles at | Average | 21.8 | 20.7 | 13.0 | 12.7 |
| the midrib (mm) | Range | (17.3-25.3) | (16.7-24.0) | (8.0-17.3) | (8.0-22.7) |

TABLE 5-continued

|  |  | ADS-26 | ADS-25 | ADS-17 | ADS-21 |
|---|---|---|---|---|---|
| Thickness of Outer Petioles at the midrib (mm) | Average | 9.3 | 9.2 | 6.9 | 6.6 |
|  | Range | (8.0-10.3) | (7.3-10.3) | (5.0-8.7) | (5.0-10.0) |
| Number of 4 inch Sticks | Average | 36.9 | 30.0 | 29.9 | 26.0 |
|  | Range | (27-42) | (24-37) | (20-39) | (19-29) |
| Weight of 4 inch Sticks (kg) | Average | 0.67 | 0.50 | 0.34 | 0.39 |
|  | Range | (0.35-0.85) | (0.25-0.67) | (0.23-0.43) | (0.31-0.50) |
| General *Fusarium* Rating |  | 5 | 4-5 | 1-2 | 2-4 |
| Root *Fusarium* Rating |  | 4 | 4 | 2 | 3 |

As shown in Table 5, under conditions of high levels of *fusarium* ADS-26 and ADS-25 showed considerably more tolerance as measured by *fusarium* ratings, plant height, trimmed plant weight, number of outer petioles, petiole length to the joint, petiole width and yield based on four inch stick count and weight. ADS-17 and ADS-21 plants were severely impacted and unmarketable. ADS-26 was more tolerant to *fusarium* compared to ADS-25 based on improved plant height, trimmed plant weight, number of outer petioles, petiole width and stick yield components (4 inch stick yield and weight).

Table 6 shows a comparison between ADS-26, ADS-25, ADS-11, ADS-21, ADS-18 and ADS-17 under conditions of moderate *fusarium* in Oxnard, Calif. that was transplanted Mar. 14, 2010 and harvested Jul. 11, 2010 at 115 days maturity. This particular trial was grown in a field that has an extremely high level of *Fusarium oxysporum* f. sp. *apii* race 2 developed for the purpose of evaluating varieties for *fusarium* tolerance. While the field had high levels of *fusarium* the conditions were less conducive to its severe expression so conditions were moderate. Table 6, column 1 shows the characteristic, column 2 shows the results for ADS-26, column 3 shows the results for ADS-25, column 4 shows the results for ADS-11, column 5 shows the results for ADS-21, column 6 shows the results for ADS-18 and column 7 shows the results for ADS-17. *Fusarium* ratings are from 0-5, where 0 indicates dead plants and 5 indicates resistant and are presented as a range of expression.

TABLE 6

|  |  | ADS-26 | ADS-25 | ADS-11 | ADS-21 | ADS-18 | ADS-17 |
|---|---|---|---|---|---|---|---|
| Plant Height (cm) | Average | 104.7 | 74.4 | 69.2 | 97.0 | 97.4 | 39.7 |
|  | Range | (101-109) | (66-82) | (47-78) | (85-105) | (89-105) | (24-50) |
| Trimmed Plant Weight (kg) | Average | 1.09 | 0.68 | 0.66 | 0.97 | 0.89 | 0.35 |
|  | Range | (0.63-1.94) | (0.38-1.09) | (0.27-1.02) | (0.63-1.40) | (0.43-1.20) | (0.21-0.52) |
| Number of Outer Petioles (>40 cm) | Average | 13.0 | 13.0 | 11.8 | 12.5 | 11.6 | 3.1 |
|  | Range | (10-15) | (10-16) | (8-15) | (10-15) | (7-15) | (0-8) |
| Number of Inner Petioles (<40 cm) | Average | 2.5 | 2.7 | 2.5 | 2.3 | 2.5 | 10.8 |
|  | Range | (2-3) | (2-3) | (0-4) | (2-3) | (2-4) | (3-16) |
| Length of Outer Petioles to the joint (cm) | Average | 48.9 | 40.5 | 37.0 | 49.1 | 49.3 | 23.1 |
|  | Range | (42.3-57.3) | (34.3-44.7) | (19.0-44.0) | (40.7-58.0) | (44.3-54.7) | (8.3-34.3) |
| Width of Outer Petioles at the midrib (mm) | Average | 19.0 | 15.6 | 15.4 | 19.6 | 19.1 | 9.4 |
|  | Range | (15.3-22.0) | (7.0-20.7) | (8.0-21.3) | (17.3-23.7) | (16.0-21.3) | (6.7-13.0) |
| Thickness of Outer Petioles at the midrib (mm) | Average | 8.8 | 7.2 | 7.5 | 9.8 | 9.1 | 5.4 |
|  | Range | (7.7-10.3) | (5.7-9.3) | (5.7-10.3) | (8.7-11.7) | (8.7-9.7) | (3.3-7.0) |
| Number of 4 inch Sticks | Average | 40.8 | 28.4 | 24.4 | 33.8 | 34.6 | * |
|  | Range | (28-50) | (18-36) | (6-36) | (21-44) | (20-47) | * |
| Weight of 4 inch Sticks (kg) | Average | 0.61 | 0.32 | 0.29 | 0.52 | 0.56 | * |
|  | Range | (0.34-1.03) | (0.16-0.55) | (0.04-0.50) | (0.31-0.78) | (0.24-0.92) | * |
| General *Fusarium* Rating |  | 5 | 4 | 2-3 | 4 | 4 | 1 |
| Root *Fusarium* Rating |  | 4 | 3.5 | 2 | 1-2 | 2-3 | 1 |
| Petiole Smoothness |  | Smooth | Slight Rib | Smooth to slight rib | Smooth | smooth | slight rib to ribby |
| Petiole Cup |  | cup | cup | cup | cup | slight cup | cup |

As shown in Table 6, ADS-26 was considerably more tolerant to *fusarium* based on *fusarium* ratings as well as yield on trimmed plant weight and four-inch stick yields compared to ADS-25, ADS-11, ADS-21, ADS-18 and ADS-17. ADS-17 was significantly impacted by *fusarium* and showed stunted height, stalk weight, joint length and outer petiole count compared to each of the other varieties. ADS-17 was 100% unmarketable and four-inch stick counts and weights were not possible (indicated by *).

Table 7 shows a comparison between ADS-26, ADS-25, ADS-18, ADS-11 and ADS-21 from a trial evaluated May 15, 2010 after exposure to 835 hours of temperature accumulation below 50° F. (severe bolting pressure). Table 7, column 1 shows the characteristic, column 2 shows the results for ADS-26, column 3 shows the results for ADS-25, column 4 shows the results for ADS-11, column 5 shows the results for ADS-18 and column 6 shows the results for ADS-21.

TABLE 7

|  |  | ADS-26 | ADS-25 | ADS-11 | ADS-18 | ADS-21 |
|---|---|---|---|---|---|---|
| Plant Height (cm) | Average | 102.9 | 94.5 | 91.3 | 100.8 | 100.9 |
|  | Range | (98-111) | (90-97) | (82-95) | (98-103) | (97-103) |
| Trimmed Plant Weight (kg) | Average | 1.01 | 0.96 | * | 0.95 | 0.93 |
|  | Range | (0.74-1.40) | (0.69-1.35) |  | (0.70-1.28) | (0.79-1.13) |
| Number of Outer Petioles (>40 cm) | Average | 8.3 | 8.0 | * | 9.2 | 9.1 |
|  | Range | (7-9) | (7-11) |  | (7-11) | (7-11) |
| Number of Inner Petioles (<40 cm) | Average | 4.3 | 4.7 | * | 4.2 | 3.2 |
|  | Range | (4-5) | (3-6) |  | (3-6) | (3-4) |
| Length of Outer Petioles to the joint (cm) | Average | 52.8 | 52.0 | * | 56.4 | 55.2 |
|  | Range | (48.3-58.7) | (48.7-59.7) |  | (52.7-60.3) | (51.7-57.7) |
| Width of Outer Petioles at the midrib (mm) | Average | 21.8 | 19.1 | * | 20.1 | 20.1 |
|  | Range | (19.7-25.3) | (15.7-21.3) |  | (17.7-22.3) | (18.3-22.0) |
| Thickness of Outer Petioles at the midrib (mm) | Average | 9.5 | 9.1 | * | 9.1 | 8.8 |
|  | Range | (8.7-10.3) | (8.3-10.3) |  | (8.0-10.0) | (8.7-9.3) |
| Number of 4 inch Sticks | Average | 30.6 | 23.4 | * | 31.0 | 33.2 |
|  | Range | (23-39) | (20-29) |  | (24-40) | (23-38) |
| Weight of 4 inch Sticks (kg) | Average | 0.56 | 0.44 | * | 0.54 | 0.57 |
|  | Range | (0.38-0.82) | (0.35-0.62) |  | (0.38-0.76) | (0.49-0.66) |
| Length of Seed Stems (cm) | Average | 0.8 | 9.9 | 24.1 | 5.9 | 0.1 |
|  | Range | (0-9) | (0-27) | (7-46) | (0-19) | (0-1.5) |
|  | Median | 0.5 | 8.5 | 22.5 | 5.0 | 0.0 |
| Petiole Smoothness |  | smooth | smooth | smooth | smooth | smooth |
| Petiole Cup |  | cup/deep | cup | cup | cup | cup |

As shown in Table 7, ADS-21 was the most tolerant for bolting with ADS-26 a fairly close second, as measured by seed stem length. ADS-18 and ADS-25 while fairly tolerant compared to ADS-11 were significantly impacted by bolting. Various trait data for ADS-11 were not able to be collected due to severe pith and brown stem associated with advanced seed stem development, indicated in the table with an asterisk (*). While ADS-21 was more bolting tolerant, ADS-26 was improved for plant height, trimmed plant weight, and width of outer petioles. ADS-21 produced more four-inch sticks but ADS-26 and ADS-21 produced essentially the same weight based yield. Under these conditions ADS-26 was most similar to ADS-21.

Table 8 shows a comparison between ADS-26, ADS-25, ADS-11, ADS-17, ADS-18 and ADS-21 under conditions of very severe bolting pressure. This trial was grown in a non traditional celery production region (Santa Paula) for the winter months in California. This is considered a non traditional production area in this season due to potential exposure to very high levels of cold hours which significantly increase the risk of bolting. This trial was evaluated Apr. 21, 2011 after 1088 hours of exposure to temperatures below 50° C. Table 8, column 1 shows the characteristic, column 2 shows the results for ADS-26, column 3 shows the results for ADS-25, column 4 shows the results for ADS-11, column 5 shows the results for ADS-17, column 6 shows the results for ADS-18 and column 7 shows the results for ADS-21.

TABLE 8

|  |  | ADS-26 | ADS-25 | ADS-11 | ADS-17 | ADS-18 | ADS-21 |
|---|---|---|---|---|---|---|---|
| Plant Height (cm) | Average | 111.0 | * | * | * | 97.2 | 102.5 |
|  | Range | (104-114) |  |  |  | (90-103) | (97-109) |
| Trimmed Plant Weight (kg) | Average | 1.03 | * | * | * | 0.94 | 1.06 |
|  | Range | (0.76-1.51) |  |  |  | (0.74-1.26) | (0.79-1.39) |
| Number of Outer Petioles (>40 cm) | Average | 9.6 | * | * | * | 9.8 | 10.1 |
|  | Range | (8-12) |  |  |  | (9-11) | (9-11) |
| Number of Inner Petioles (<40 cm) | Average | 4.1 | * | * | * | 5.7 | 4.1 |
|  | Range | (3-5) |  |  |  | (5-7) | (3-5) |
| Length of Outer Petioles to the joint (cm) | Average | 57.9 | 51.5 | 41.5 | 56.4 | 55.2 | 58.0 |
|  | Range | (50-63) | (46.3-54.0) | (35.3-45.0) | (53.7-60.3) | (48-60) | (53.7-60.7) |
| Width of Outer Petioles at the midrib (mm) | Average | 19.2 | * | * | * | 18.7 | 21.1 |
|  | Range | (17.7-21.0) |  |  |  | (16.3-22.3) | (19.0-22.7) |
| Thickness of Outer Petioles at the midrib (mm) | Average | 7.9 | * | * | * | 8.0 | 9.2 |
|  | Range | (7.0-9.3) |  |  |  | (6.7-9.7) | (7.7-10.0) |
| Number of 4 inch Sticks | Average | 34.8 | * | * | * | 34.4 | 36.4 |
|  | Range | (26-42) |  |  |  | (28-40) | (33-40) |
| Weight of 4 inch Sticks (kg) | Average | 0.56 | * | * | * | 0.49 | 0.56 |
|  | Range | (0.43-0.80) |  |  |  | (0.33-0.69) | (0.45-0.74) |
| Length of Seed Stems (cm) | Average | 10.6 | 22.6 | 37.4 | 37.0 | 15.5 | 4.1 |
|  | Range | (0.5-77.0) | (14-31) | (12-57) | (23-51) | (6-23) | (0-10) |
|  | Median | 2.5 | 21.0 | 42.0 | 38.0 | 16.0 | 3.0 |
| Petiole Color (Munsell Color Chart) |  | 5gy 7/6 | * | * | * | 5gy 6/6 | 5gy 6/6 |

TABLE 8-continued

|  | ADS-26 | ADS-25 | ADS-11 | ADS-17 | ADS-18 | ADS-21 |
|---|---|---|---|---|---|---|
| Leaf Color (Munsell Color Chart) | 5gy 4/4 | * | * | * | 5gy 4/4 | 5gy 4/4 |
| Petiole Smoothness | rib | * | * | * | slight rib | smooth/slight rib |
| Petiole Cupping | cup | * | * | * | cup | cup |
| Brown Stem | 70% | 100% | 100% | 100% | 100% | 0% |

As shown in Table 8, under these colder conditions, which promote bolting, ADS-11, ADS-17 and ADS-25 demonstrated more susceptibility to bolting, based on seed stem length. These conditions also promoted numerous defects which cause distortion for the various other characteristics traditionally measured so there are many traits which do not have measurements marked by an '*'. Of the three susceptible, ADS-25 performed slightly better than ADS-11 and ADS-17 based on slightly smaller seed stem development and longer petioles measured at the joint. ADS-21 was considerably more tolerant for bolting compared to all varieties but ADS-26 was the second most tolerant as measured by seed stem length. However, under these conditions ADS-26 was still not tolerant enough for production. While more bolting tolerant than ADS-18, ADS-26 was fairly similar to it for number of outer petioles, width, thickness of petioles and number of four-inch sticks. ADS-26 was more similar to ADS-21 for weight, petiole length and finished weight of four-inch sticks.

Table 9 shows a comparison between ADS-26, ADS-25, ADS-4 and ADS-17 grown in Salinas, Calif. under conditions free from disease and bolting pressure. The trial was transplanted Apr. 30, 2011 and harvested Jul. 26, 2011 and was evaluated at 87 days. The plant population was 52,800 plants per acre. Table 9, column 1 shows the characteristic, column 2 shows the results for ADS-26, column 3 shows the results for ADS-25, column 4 shows the results for ADS-4 and column 5 shows the results for ADS-17.

TABLE 9

|  |  | ADS-26 | ADS-25 | ADS-4 | ADS-17 |
|---|---|---|---|---|---|
| Plant Height (cm) | Average | 100.4 | 91.5 | 87.6 | 98.4 |
|  | Range | (97-105) | (85-97) | (85-91) | (95-104) |
| Trimmed Plant Weight (kg) | Average | 1.02 | 0.95 | 1.00 | 1.17 |
|  | Range | (0.83-1.19) | (0.71-1.24) | (0.85-1.12) | (0.98-1.58) |
| Number of Outer Petioles (>40 cm) | Average | 9.8 | 9.9 | 11.3 | 10.7 |
|  | Range | (9-11) | (9-11) | (10-13) | (9-12) |
| Number of Inner Petioles (<40 cm) | Average | 2.6 | 2.8 | 3.3 | 3.2 |
|  | Range | (2-3) | (2-3) | (3-4) | (2-4) |
| Length of Outer Petioles to the joint (cm) | Average | 51.7 | 47.4 | 46.7 | 55.6 |
|  | Range | (47.3-54.3) | (43.7-51.3) | (42.3-52.7) | (51.3-61.3) |
| Width of Outer Petioles at the midrib (mm) | Average | 18.0 | 18.9 | 18.1 | 19.7 |
|  | Range | (17.0-18.7) | (17.0-20.3) | (17.0-19.7) | (17.7-22.3) |
| Thickness of Outer Petioles at the midrib (mm) | Average | 8.6 | 8.6 | 8.3 | 9.4 |
|  | Range | (8.0-9.3) | (7.0-9.7) | (7.3-9.0) | (6.3-10.7) |
| Number of 4 inch Sticks | Average | 36.9 | 31.9 | 36.1 | 43.3 |
|  | Range | (33-40) | (25-39) | (34-39) | (38-55) |
| Weight of 4 inch Sticks (kg) | Average | 0.58 | 0.49 | 0.55 | 0.68 |
|  | Range | (0.45-0.68) | (0.34-0.68) | (0.46-0.60) | (0.54-0.85) |

As shown in Table 9, except for plant height and number of outer petioles, ADS-17 outperformed ADS-25, ADS-4 and ADS-26 for all other characteristics including yield based on four-inch stick count and weight. Under the summer conditions in Salinas, ADS-26 was more similar to ADS-4 for plant weight, petiole thickness, number and weight of four-inch sticks and similar to ADS-25 for the number of outer petioles.

Table 10 shows larger test production comparisons between cultivars ADS-26, ADS-25 and ADS-11 in Oxnard, Calif. The three varieties were grown in adjacent blocks at intermediate plant populations of 58,080 plants per acre and harvested as whole stalks with the tops trimmed to approximately 22 to 24 inches and then inserted into totes. These totes were then counted, and weighed to get a yield in totes per acre and gross pounds per acre. The totes were then transported to the processing facility where they were cut into 4 inch sticks utilizing a water jet cutter and then sorted and packaged. The finished yield was then determined following processing and presented as net pounds per acre. Efficiency is calculated as a percentage of usable product. There were no prominent weather events and fairly weak *fusarium* expression in these production blocks. Table 10, column 1 shows the characteristic, column 2 shows the results for ADS-26, column 3 shows the results for ADS-25 and column 4 shows the results for ADS-11.

TABLE 10

| Characteristic | ADS-26 | ADS-25 | ADS-11 |
|---|---|---|---|
| Harvest date | Nov. 18, 2012 | Nov. 18, 2012 | Nov. 18, 2012 |
| Plant population | 58,080 | 58,080 | 58,080 |
| Maturity days | 110 | 110 | 110 |
| Total Acres Harvested | 1.00 | 1.00 | 1.25 |
| Yield in Totes per Acre | 1,702 | 1,680 | 1,575 |

TABLE 10-continued

| Characteristic | ADS-26 | ADS-25 | ADS-11 |
|---|---|---|---|
| Average Tote Weight (pounds) | 54 | 55 | 53 |
| Gross Pounds per Acre | 91,908 | 92,400 | 83,475 |

TABLE 10-continued

| Characteristic | ADS-26 | ADS-25 | ADS-11 |
|---|---|---|---|
| Net Pounds per Acre (4 inch sticks) | 44,116 | 49,896 | 40,903 |
| Efficiency | 48% | 54% | 49% |

As shown in Table 10, while ADS-26 produced more totes per acre, the slightly smaller petioles and taller celery stalks trimmed to 22 to 24 inches in order to fit the totes had a net effect of reducing the yield of ADS-26 compared to ADS-25. The limitation of the size of the totes had a net effect of reducing potential yield for ADS-26. ADS-11 was slightly impacted by *fusarium* and performed poorer based on overall yield as measured by the number of totes, gross and finished pounds (net pounds) per acre.

Table 11 shows larger test production comparisons between cultivars ADS-26, ADS-25 and ADS-11 in Oxnard, Calif. The three varieties were grown in adjacent blocks at intermediate plant populations of 58,080 plants per acre and harvested as whole stalks with the tops trimmed to approximately 22 to 24 inches and then inserted in totes. These totes were then counted, and weighed to get a yield in totes per acre and gross pounds per acre. The totes were then transported to the processing facility where they were cut into 4 inch sticks utilizing a water jet cutter and then sorted and packaged. The finished yield was then determined following processing and presented as net pounds per acre. Efficiency is calculated as a percentage of usable product. These blocks were exposed to a fairly strong Santa Ana wind event which caused some lodging, wind damage and secondary brown stem. Table 11, column 1 shows the characteristic, column 2 shows the results for ADS-26, column 3 shows the results for ADS-25 and column 4 shows the results for ADS-11.

TABLE 11

| Characteristic | ADS-26 | ADS-25 | ADS-11 |
|---|---|---|---|
| Harvest date | Nov. 10, 2012 | Nov. 10, 2012 | Nov. 10, 2012 |
| Plant population | 58,080 | 58,080 | 58,080 |
| Maturity days | 112 | 112 | 112 |
| Lodging (% plants impacted) | 27% | 0% | 0% |
| Brown Stem (% plants impacted) | 15% | 0% | 2% |
| Total Acres Harvested | 0.50 | 1.00 | 1.00 |
| Yield in Totes per Acre | 1,425 | 1,675 | 1,500 |
| Average Tote Weight (pounds) | 49 | 55 | 50 |
| Gross Pounds per Acre | 69,825 | 92,125 | 75,000 |
| Net Pounds per Acre (4 inch sticks) | 35,611 | 56,196 | 39,750 |
| Efficiency | 51% | 61% | 53% |

As shown in Table 11, while there was slight *fusarium* present ADS-25 proved to be fairly tolerant to lodging and subsequent brown stem following lodging damage, whereas ADS-11 had a slight yield decrease. However, the taller more vigorous ADS-26 experienced more lodging and associated yield loss and subsequent brown stem in busted and cracked petioles associated with the wind damage.

Table 12 shows the results of a larger test production comparison between cultivars ADS-26, ADS-25 and ADS-11 in Oxnard, Calif. that was harvested Jan. 24 to 25, 2013. The three varieties were grown in adjacent blocks at an intermediate plant population of 58,080 plants per acre and harvested as whole stalks with the tops trimmed to approximately 22 to 24 inches and then inserted into totes. These totes were then counted, and weighed to get a yield in totes per acre and gross pounds per acre. The totes were then transported to the processing facility where they were cut into four-inch sticks utilizing a water jet cutter and then sorted and packaged. The finished yield was then determined following processing and presented as net pounds per acre. Efficiency is calculated as a percentage of usable product. These blocks were exposed to a fairly strong freeze event which caused some damage including blister of the epidermis on some petioles and brown stem in the subsequent damaged petioles. Table 12, column 1 shows the characteristic, column 2 shows the results for ADS-26, column 3 shows the results for ADS-25 and column 4 shows the results for ADS-11.

TABLE 12

| Characteristic | ADS-26 | ADS-25 | ADS-11 |
|---|---|---|---|
| Harvest date | Jan. 25, 2013 | Jan. 24, 2013 | Jan. 24, 2013 |
| Plant population | 58,080 | 58,080 | 58,080 |
| Maturity days | 120 | 119 | 119 |
| Brown Stem (% plants impacted) | 13% | 0% | 2% |
| Total Acres Harvested | 0.80 | 2.20 | 0.75 |
| Yield in Totes per Acre | 1,431 | 1,645 | 1,500 |
| Average Tote Weight (pounds) | 49 | 52 | 51 |
| Gross Pounds per Acre | 70,119 | 85,540 | 76,500 |
| Net Pounds per Acre (4 inch sticks) | 28,749 | 40,204 | 34,425 |
| Efficiency | 41% | 47% | 45% |

As shown in Table 12, the worst damage occurred to ADS-26 which is more erect and has less foliage providing protection from freeze conditions (the freeze blistered the petioles more directly). ADS-25 and ADS-11 had very little impact from the freezing conditions and out yielded ADS-26, which required removal of more damaged petioles.

Table 13 shows the results of a larger test production comparison between cultivars ADS-26, ADS-25 and ADS-11 harvested in Oxnard, Calif. from Feb. 19 to 21, 2013. The three varieties were grown in adjacent blocks at an intermediate plant population of 58,080 plants per acre and harvested as whole stalks with the tops trimmed to approximately 22 to 24 inches and then inserted into totes. These totes were then counted, and weighed to get a yield in totes per acre and gross pounds per acre. The totes were then transported to the processing facility where they were cut into 4 inch sticks utilizing a water jet cutter and then sorted and packaged. The finished yield was then determined following processing and presented as net pounds per acre. Efficiency is calculated as a percentage of usable product. The production was free of any particular adverse production events. Table 13, column 1 shows the characteristic, column 2 shows the results for ADS-26, column 3 shows the results for ADS-25 and column 4 shows the results for ADS-11.

TABLE 13

| Characteristic | ADS-26 | ADS-25 | ADS-11 |
|---|---|---|---|
| Harvest date | Feb. 20, 2013 | Feb. 21, 2013 | Feb. 19, 2013 |
| Plant population | 58,080 | 58,080 | 58,080 |
| Maturity days | 118 | 119 | 117 |
| Total Acres Harvested | 2.22 | 0.43 | 1.20 |
| Yield in Totes per Acre | 1,720 | 1,702 | 1,545 |

TABLE 13-continued

| Characteristic | ADS-26 | ADS-25 | ADS-11 |
|---|---|---|---|
| Average Tote Weight (pounds) | 57 | 57 | 55 |
| Gross Pounds per Acre | 98,040 | 97,014 | 84,975 |
| Net Pounds per Acre (4 inch sticks) | 57,844 | 55,298 | 48,436 |
| Efficiency | 59% | 57% | 57% |

As shown in Table 13, ADS-26 not only out yielded ADS-25 and ADS-11, but had the highest efficiency.

Table 14 shows the results of a large production grow out for comparing cultivars ADS-26 and ADS-25 that was harvested in Oxnard, Calif. from Nov. 20 to 21, 2012. These cultivars were grown in adjacent blocks at an intermediate plant population of 58,080 plants per acre and harvested as whole stalks with the tops trimmed to approximately 22 to 24 inches and then inserted into totes. These totes were then counted, and weighed to get a yield in totes per acre and gross pounds per acre. The totes were then transported to the processing facility where they were cut into various different products. Since different finished products were created yield comparisons were limited to gross weight per acre. These blocks were exposed to a fairly strong Santa Ana wind event which caused some lodging, wind damage and secondary brown stem. Table 14, column 1 shows the characteristic, column 2 shows the results for ADS-26 and column 3 shows the results for ADS-25.

TABLE 14

| Characteristic | ADS-26 | ADS-25 |
|---|---|---|
| Harvest date | Nov. 21, 2012 | Nov. 20, 2012 |
| Plant population | 58,080 | 58,080 |
| Maturity days | 109 | 111 |
| Total Acres Harvested | 4.87 | 6.03 |
| Yield in Totes per Acre | 1,250 | 1,455 |
| Average Tote Weight (pounds) | 52 | 54 |
| Gross Pounds per Acre | 65,000 | 78,570 |

As shown in Table 14, ADS-25 had higher gross pounds per acre when compared to ADS-26. While there was slight *fusarium* present, both varieties were relatively tolerant so the impact was minimal. However, the taller more vigorous ADS-26 experienced more lodging and associated yield loss and subsequent brown stem in busted and cracked petioles associated with the wind damage.

The use of the terms "a," "an," and "the," and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

DEPOSIT INFORMATION

A deposit of the A. Duda & Sons, Inc. proprietary CELERY CULTIVAR ADS-26 disclosed above and recited in the appended claims has been made with the American Type Culture Collection (ATCC), 10801 University Boulevard, Manassas, Va. 20110. The date of deposit was Oct. 30, 2014. The deposit of 2,500 seeds was taken from the same deposit maintained by A. Duda & Sons, Inc. since prior to the filing date of this application. All restrictions will be irrevocably removed upon granting of a patent, and the deposit is intended to meet all of the requirements of 37 C.F.R. §§1.801-1.809. The ATCC Accession Number is PTA-121683. The deposit will be maintained in the depository for a period of thirty years, or five years after the last request, or for the enforceable life of the patent, whichever is longer, and will be replaced as necessary during that period.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

What is claimed is:

1. A seed of celery cultivar ADS-26, wherein a representative sample seed of said cultivar was deposited under ATCC Accession No. PTA-121683.

2. A celery plant, or a part thereof, produced by growing the seed of claim 1.

3. A tissue culture produced from protoplasts or cells from the plant of claim 2, wherein said cells or protoplasts are produced from a plant part selected from the group consisting of leaf, callus, pollen, ovule, embryo, cotyledon, hypocotyl, meristematic cell, root, root tip, pistil, anther, flower, seed, shoot, stem, petiole and sucker.

4. A celery plant regenerated from the tissue culture of claim 3, wherein said regenerated plant comprises all of the morphological and physiological characteristics of celery cultivar ADS-26 listed in Table 1.

5. A method for producing a celery seed, said method comprising crossing two celery plants and harvesting the resultant celery seed, wherein at least one celery plant is the celery plant of claim 2.

6. An $F_1$ celery seed produced by the method of claim 5.

7. An $F_1$ celery plant, or a part thereof, produced by growing said seed of claim 6.

8. The method of claim 5, wherein at least one of said celery plants is transgenic.

9. A method of producing a herbicide resistant celery plant, wherein said method comprises introducing a gene conferring herbicide resistance into the plant of claim 2.

10. A herbicide resistant celery plant produced by the method of claim 9, wherein the gene confers resistance to a herbicide selected from the group consisting of glyphosate, sulfonylurea, imidazolinone, dicamba, glufosinate, phenoxy proprionic acid, L-phosphinothricin, cyclohexone, cyclohexanedione, triazine, and benzonitrile, wherein said plant comprises all of the physiological and morphological characteristics of celery cultivar ADS-26.

11. A method of producing a pest or insect resistant celery plant, wherein said method comprises introducing a gene conferring pest or insect resistance into the celery plant of claim 2.

12. A pest or insect resistant celery plant produced by the method of claim 11, wherein said plant comprises all of the physiological and morphological characteristics of celery cultivar ADS-26.

13. The celery plant of claim 12, wherein the gene encodes a *Bacillus thuringiensis* (Bt) endotoxin, wherein said plant comprises all of the physiological and morphological characteristics of celery cultivar ADS-26.

14. A method of producing a disease resistant celery plant, wherein said method comprises introducing a gene into the celery plant of claim 2.

15. A disease resistant celery plant produced by the method of claim 14, wherein said plant comprises all of the physiological and morphological characteristics of celery cultivar ADS-26.

16. A method for producing a male sterile celery plant, wherein said method comprises transforming the celery plant of claim 2 with a nucleic acid molecule that confers male sterility.

17. A male sterile celery plant produced by the method of claim 16, wherein said plant comprises all of the physiological and morphological characteristics of celery cultivar ADS-26.

18. A method of introducing a desired trait into celery cultivar ADS-26, wherein the method comprises:
(a) crossing a ADS-26 plant, wherein a representative sample of seed was deposited under ATCC Accession No. PTA-121683, with a plant of another celery cultivar that comprises a desired trait to produce progeny plants, wherein the desired trait is selected from the group consisting of improved nutritional quality, industrial usage, male sterility, herbicide resistance, insect resistance, modified seed yield, modified lodging resistance, modified iron-deficiency chlorosis and resistance to bacterial disease, fungal disease or viral disease;
(b) selecting one or more progeny plants that have the desired trait to produce selected progeny plants;
(c) backcrossing the selected progeny plants with the ADS-26 plants to produce backcross progeny plants;
(d) selecting for backcross progeny plants that have the desired trait; and
(e) repeating steps (c) and (d) two or more times in succession to produce selected third or higher backcross progeny plants that comprise the desired trait.

19. A celery plant produced by the method of claim 18, wherein the plant has the desired trait and all of the physiological and morphological characteristics of celery cultivar ADS-26.

20. The celery plant of claim 19, wherein the desired trait is herbicide resistance and the resistance is conferred to a herbicide selected from the group consisting of imidazolinone, dicamba, cyclohexanedione, sulfonylurea, glyphosate, glufosinate, phenoxy proprionic acid, L-phosphinothricin, triazine and benzonitrile.

21. The celery plant of claim 19, wherein the desired trait is insect resistance and the insect resistance is conferred by a gene encoding a *Bacillus thuringiensis* endotoxin.

22. The celery plant of claim 19, wherein the desired trait is male sterility and the trait is conferred by a cytoplasmic nucleic acid molecule.

23. A method of producing a celery plant with modified fatty acid metabolism or modified carbohydrate metabolism comprising transforming the celery plant of claim 2 with a transgene encoding a protein selected from the group consisting of fructosyltransferase, levansucrase, α-amylase, invertase and starch branching enzyme or DNA encoding an antisense of stearyl-ACP desaturase.

24. A celery plant having modified fatty acid metabolism or modified carbohydrate metabolism produced by the method of claim 23, wherein said plant comprises all of the physiological and morphological characteristics of celery cultivar ADS-26.

* * * * *